(12) United States Patent
Okumura et al.

(10) Patent No.: US 8,491,498 B2
(45) Date of Patent: Jul. 23, 2013

(54) SAMPLE COLLECTION IMPLEMENT

(75) Inventors: Koji Okumura, Kyoto (JP); Toshihiko Harada, Kyoto (JP); Kazuya Iketani, Kyoto (JP); Masafumi Koike, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 0 days.

(21) Appl. No.: 12/737,700

(22) PCT Filed: Aug. 27, 2009

(86) PCT No.: PCT/JP2009/064953
§ 371 (c)(1),
(2), (4) Date: Feb. 8, 2011

(87) PCT Pub. No.: WO2010/026913
PCT Pub. Date: Mar. 11, 2010

(65) Prior Publication Data
US 2011/0130681 A1    Jun. 2, 2011

(30) Foreign Application Priority Data

| Sep. 8, 2008 | (JP) | 2008-229390 |
| Sep. 8, 2008 | (JP) | 2008-229391 |
| Sep. 8, 2008 | (JP) | 2008-229392 |
| Sep. 8, 2008 | (JP) | 2008-229393 |

(51) Int. Cl.
*A61B 10/00* (2006.01)
*A61B 5/00* (2006.01)
*B01D 35/00* (2006.01)
*B01D 41/00* (2006.01)

(52) U.S. Cl.
USPC .......................... 600/572; 600/573; 422/534

(58) Field of Classification Search
USPC .. 600/562, 569, 570, 572, 573, 580; 604/317; 210/359; 422/534 X, 535 X
See application file for complete search history.

(56) References Cited

U.S. PATENT DOCUMENTS

| 3,661,265 A | * | 5/1972 | Greenspan | 210/359 |
| 3,819,045 A | * | 6/1974 | Greenwald | 436/178 |
| 5,358,690 A | * | 10/1994 | Guirguis | 422/420 |
| 5,543,115 A | * | 8/1996 | Karakawa | 422/535 |

FOREIGN PATENT DOCUMENTS

| JP | 6-148177 A | 5/1944 |
| JP | 5-92724 U | 12/1993 |
| JP | 6-324037 A | 11/1994 |
| JP | 6-331625 A | 12/1994 |

(Continued)

OTHER PUBLICATIONS

International Search Report mailed on Nov. 17, 2009.

*Primary Examiner* — Max Hindenburg
*Assistant Examiner* — Jonathan M Foreman
(74) *Attorney, Agent, or Firm* — Fox Rothschild LLP

(57) ABSTRACT

A sample collection implement S1 includes a container 1 having an accommodation portion 10 in which a liquid 5 for suspending or diluting a sample is accommodated, a sample collection stick 2 being able to be disposed in the accommodation portion 10, a filter 3 provided inside the container 1, and a movable member 4 that can be moved in a predetermined direction inside the container 1 and has a function of pushing the liquid 5 and causing the liquid to pass through the filter 3, when moved in the predetermined direction. With such a configuration, when the liquid 5 is filtered, it is not necessary to move the filter 3 by directly pushing it and a filter with a low mechanical strength can be used as the filter 3. In addition, it is not necessary to use a centrifugal apparatus.

12 Claims, 22 Drawing Sheets

FOREIGN PATENT DOCUMENTS

| | | |
|---|---|---|
| JP | 8-050131 A | 2/1996 |
| JP | 8-075730 A | 3/1996 |
| JP | 8-160040 A | 6/1996 |
| JP | 9-089887 A | 4/1997 |
| JP | 10-13698 A | 1/1998 |
| JP | 10-160728 A | 6/1998 |
| JP | 10-257881 A | 9/1998 |
| JP | 11-183469 A | 7/1999 |
| JP | 2000-193660 A | 7/2000 |
| JP | 2000-258308 A | 9/2000 |
| JP | 2004-125546 A | 4/2004 |
| JP | 2005-114654 A | 4/2005 |
| JP | 2005-114654 A | 4/2005 |
| JP | 3718017 B2 | 12/2005 |
| JP | 2006-105770 A | 4/2006 |
| JP | 2007-127436 A | 5/2007 |
| JP | 2007-170979 A | 7/2007 |

\* cited by examiner

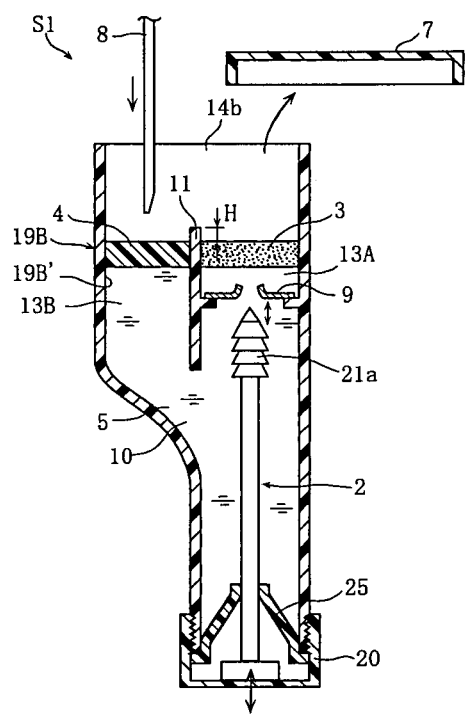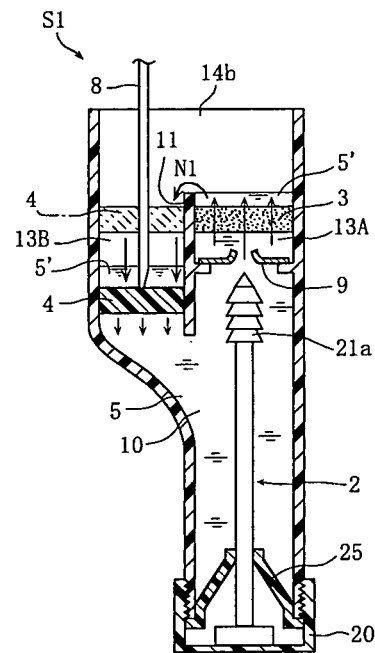
FIG. 4A
FIG. 4B

FIG. 5A
FIG. 5B
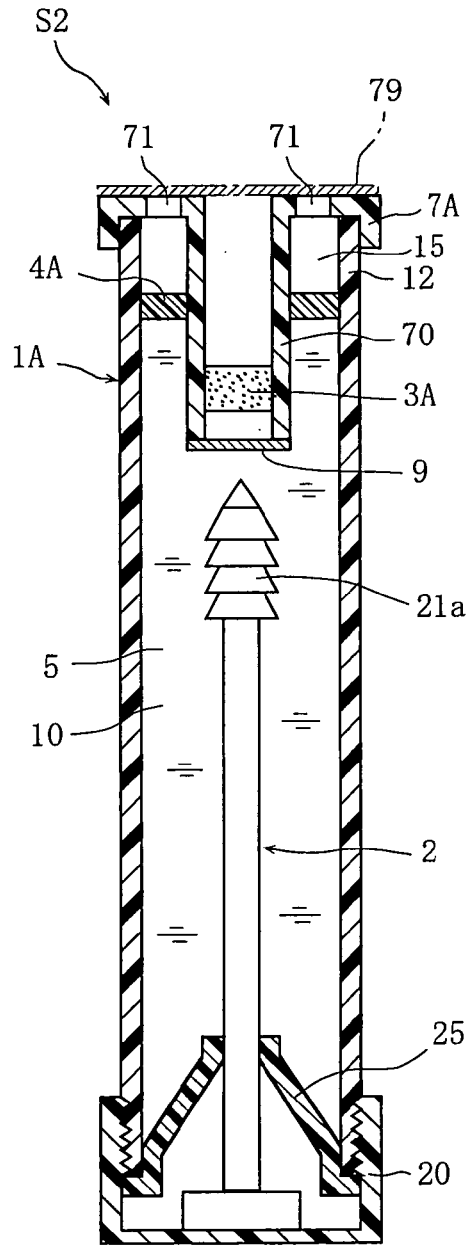
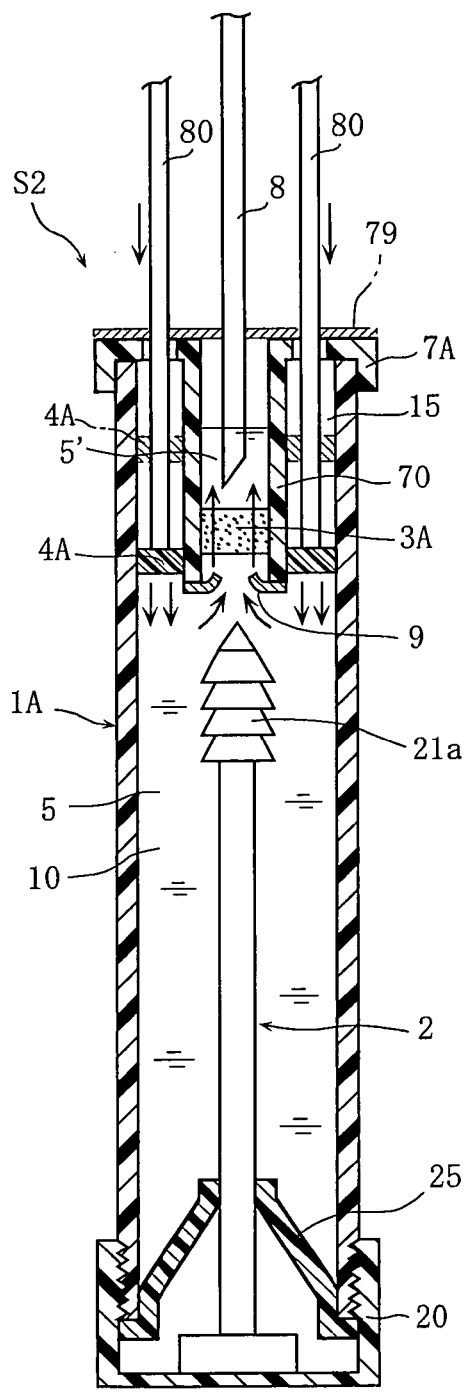

FIG. 6A
FIG. 6B
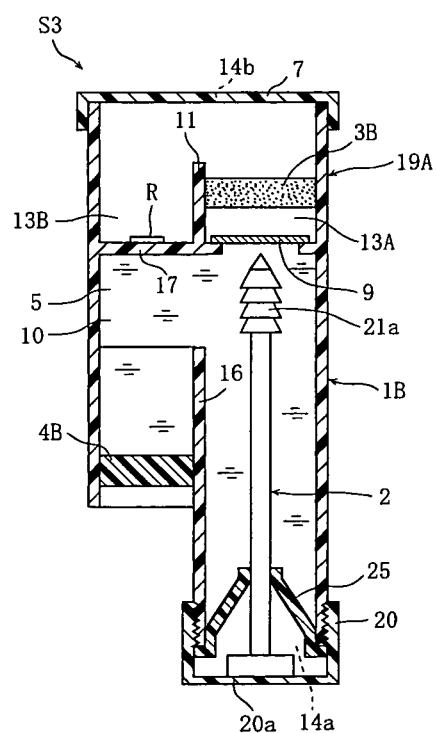
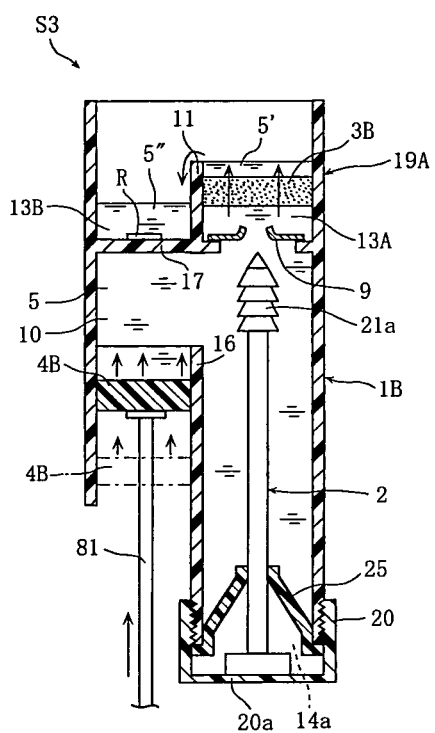

FIG. 10
FIG. 10A
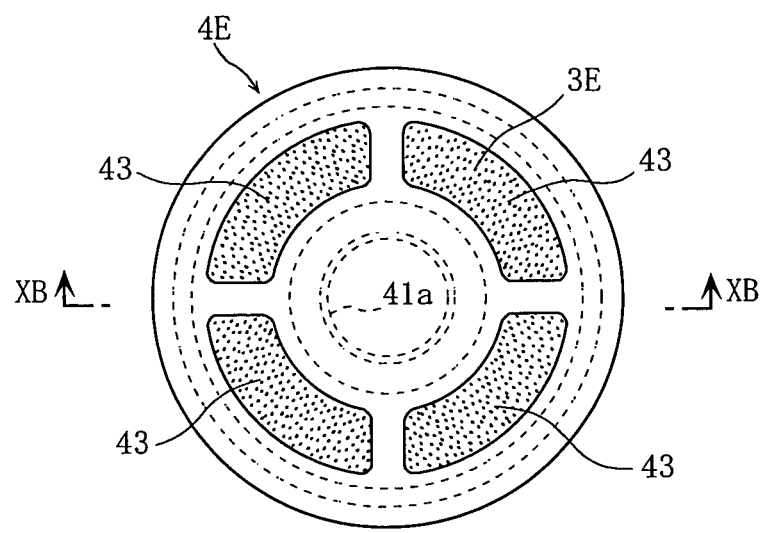
FIG. 10B
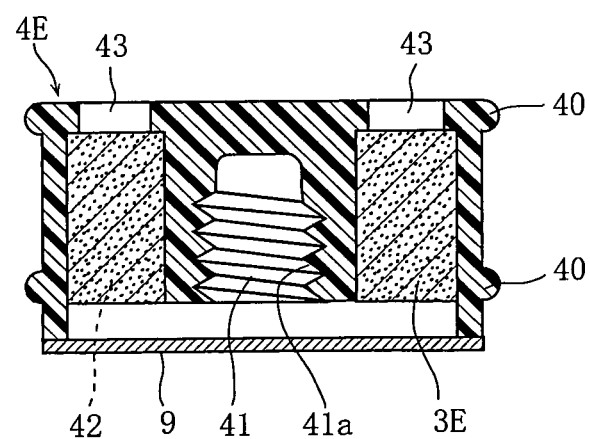

FIG. 11A
FIG. 11B
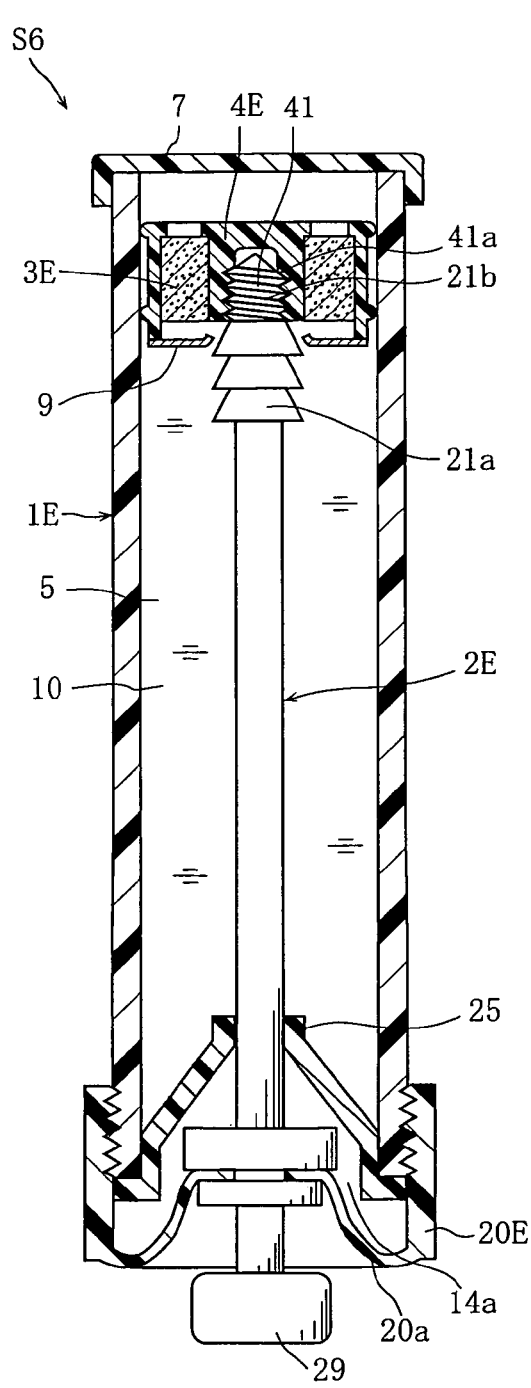
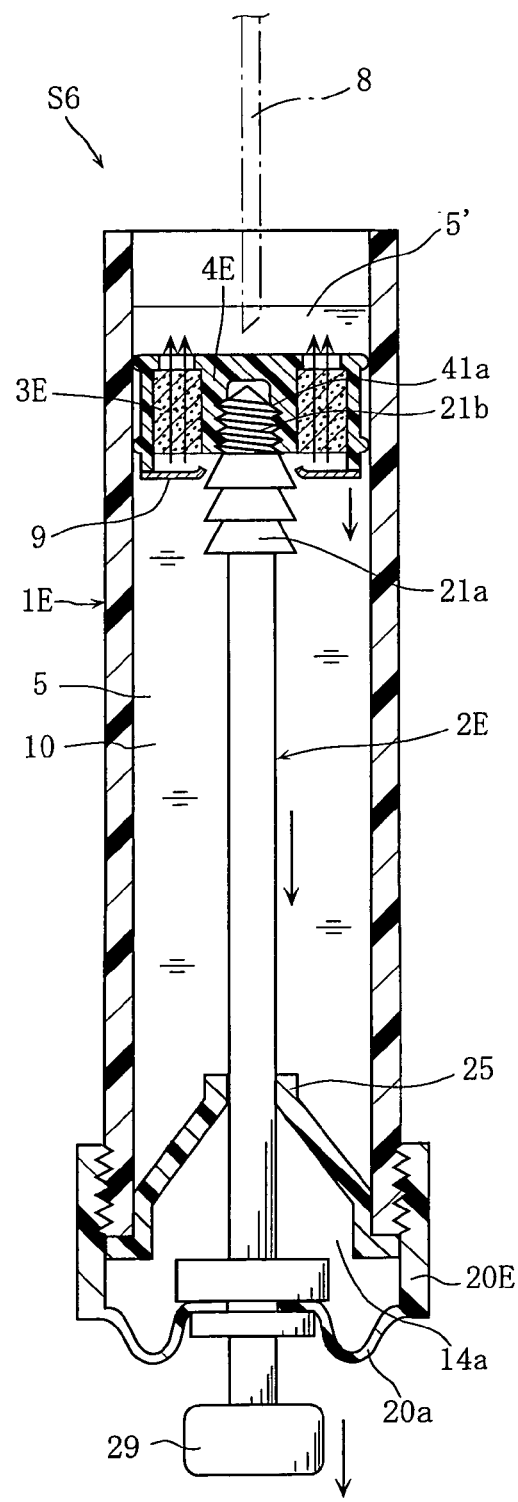

FIG. 13A
FIG. 13B
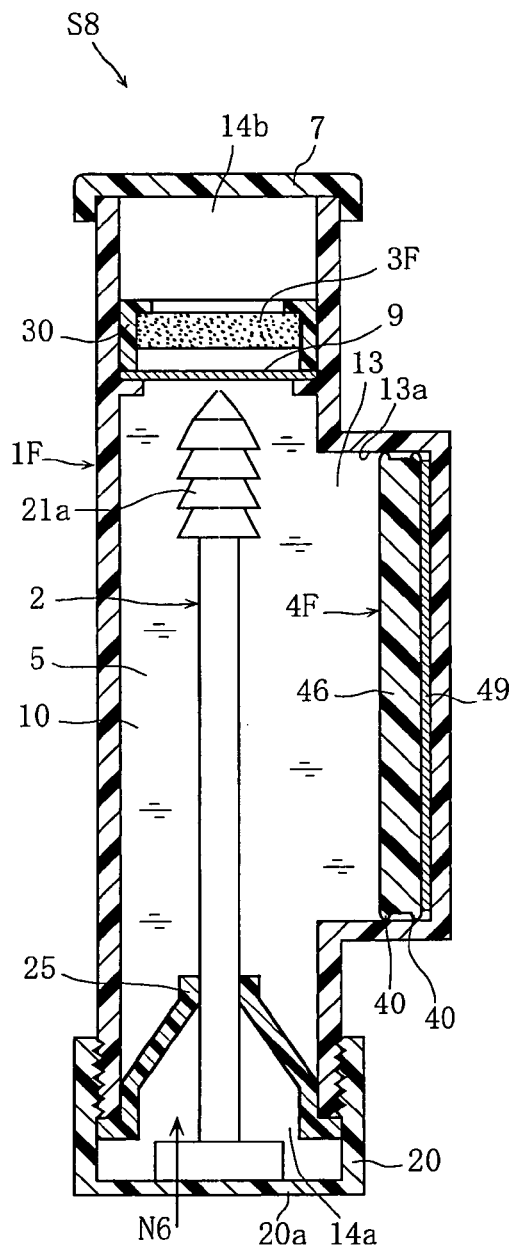
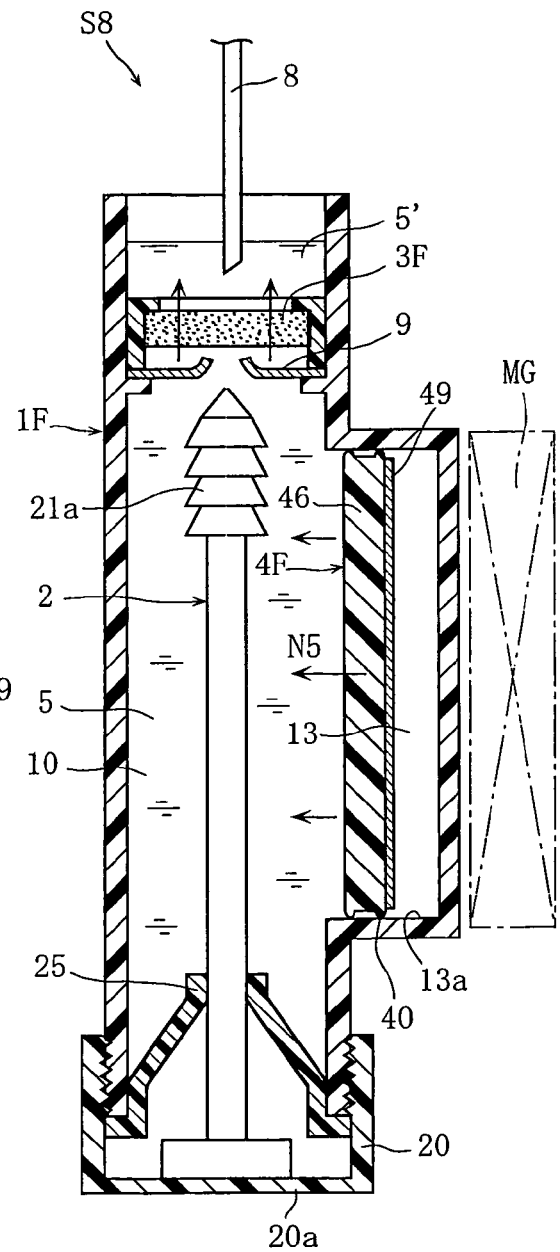

FIG. 18A
FIG. 18B
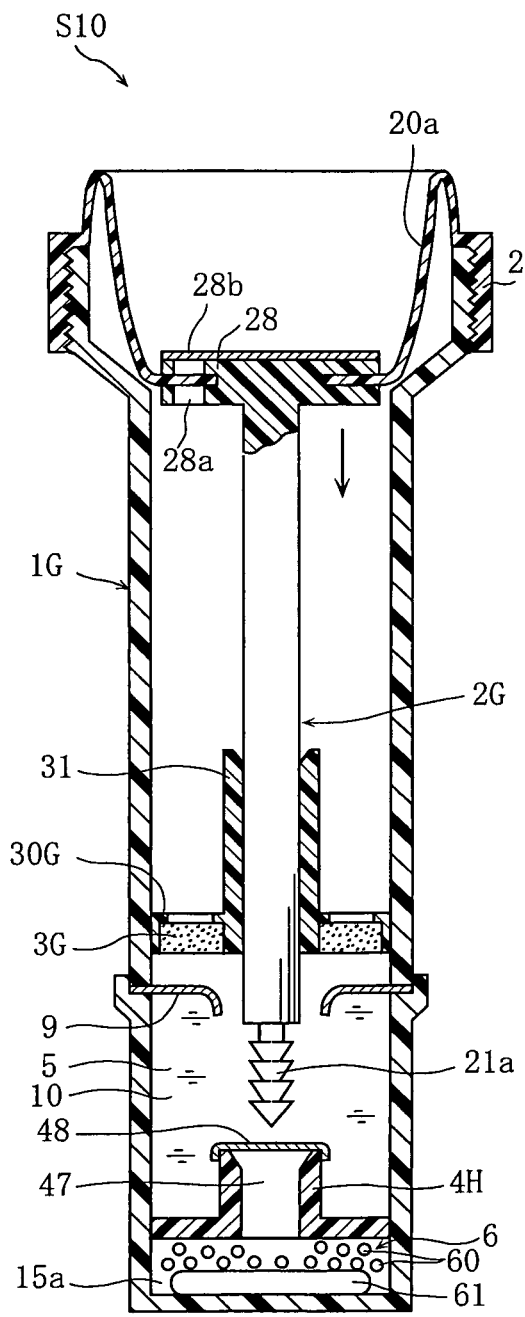
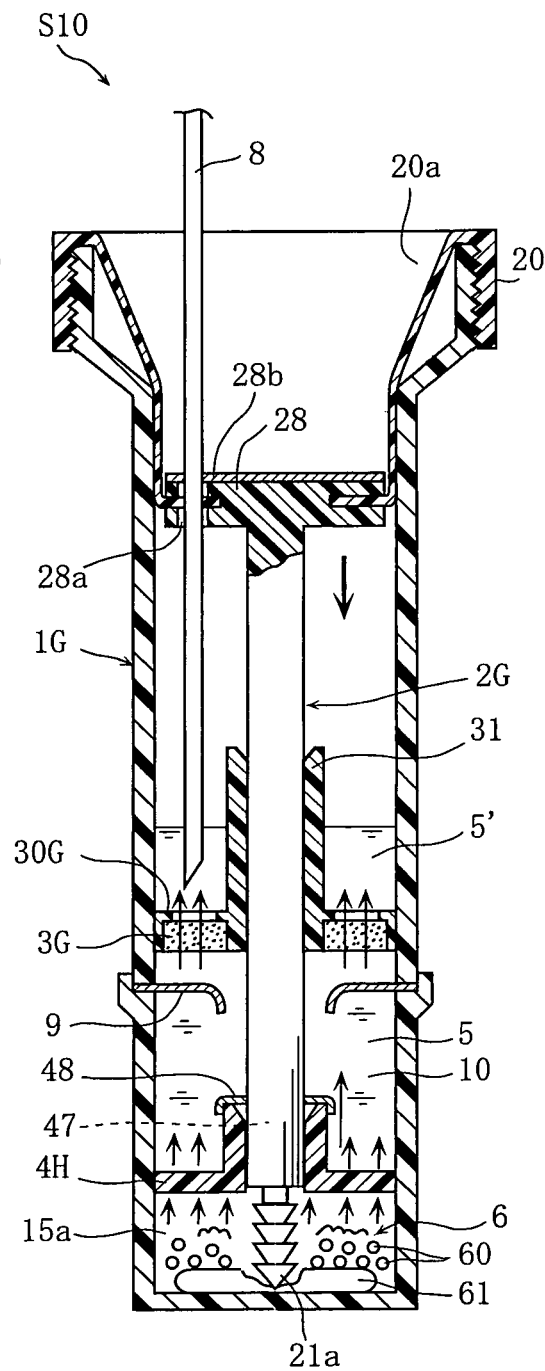

FIG. 24A
FIG. 24B
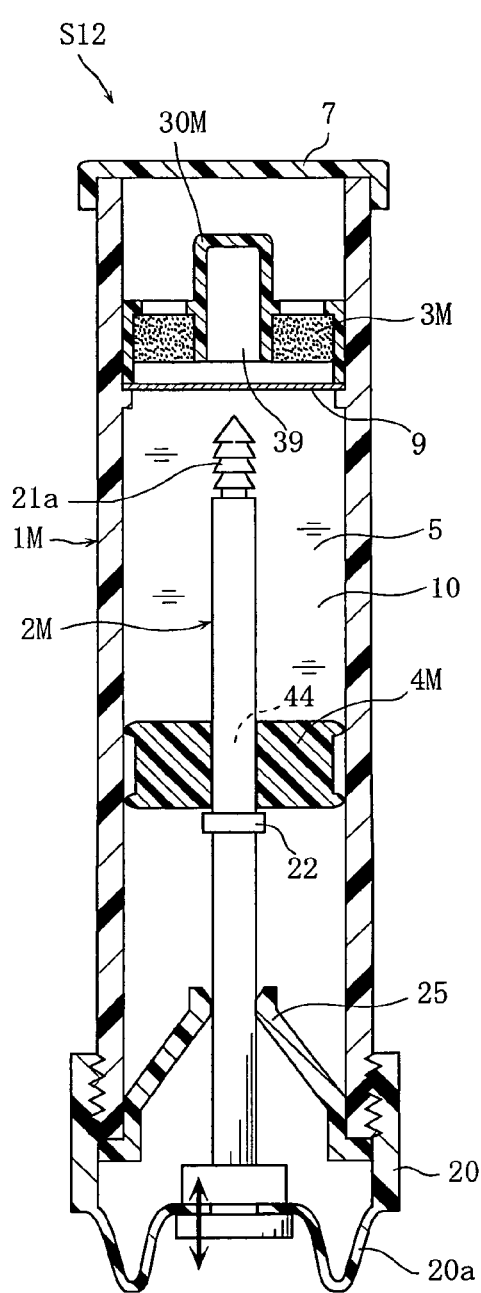
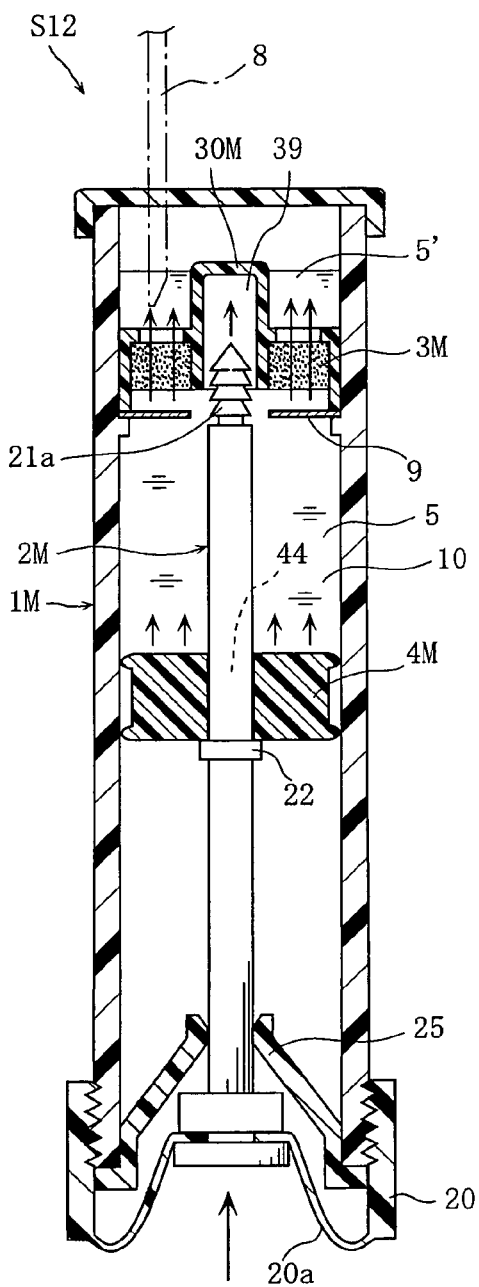

SAMPLE COLLECTION IMPLEMENT

TECHNICAL FIELD

The present invention relates to a sample collection implement for use in collecting a sample such as feces for examination.

BACKGROUND ART

Specific examples of sample collection implements are described in Patent Documents 1 to 3. The sample collection implements described in these documents are all feces collection implements and include a container accommodating a liquid for suspending the feces, a feces collection stick, and a filter. The feces collection stick can be inserted into the container, and the feces collected by the feces collection stick are caused to diffuse into the liquid by this insertion operation. The filter serves to filter the liquid into which the feces have diffused (feces suspension) and remove the solid component of the feces present in the liquid. The liquid filtered by the filter is sucked in, for example, by a suction nozzle of an automatic analyzer and supplied for analysis.

As an example of a means for filtering the liquid by using the filter, Patent Document 1 describes bringing the suction nozzle of the automatic analyzer into contact with the filter and pushing the filter into the container by using the suction nozzle. In the configuration described in Patent Document 2, the filter is held in a cylindrical member and the cylindrical member is slidably fitted into the container. Where the cylindrical member is caused to slide and the filter is pushed into the container, the liquid passes through the filter. In the configuration described in Patent Document 3, a centrifugal apparatus is used as a means for filtering the liquid. Where a sample collection implement is set into the centrifugal apparatus and rotated at a high speed, the liquid is caused by the centrifugal force to pass through the filter.

However, the following drawbacks are associated with the above-described conventional technology.

Thus, in the configuration described in Patent Document 1, when the filter is pushed into the container by using the suction nozzle of the automatic analyzer, the suction nozzle comes into direct contact with the filter. In this case, the filter can be damaged by contact with the suction nozzle, thereby making it impossible to push the filter adequately into the container. Even if the filter has been pushed into the container, since a damaged portion has appeared in the filter, the liquid (feces suspension) can pass directly through the damaged portion and the liquid cannot be filtered adequately. For this reason, in the configuration described in Patent Document 1, a material that has a high mechanical strength and cannot be easily damaged should be used as the filter and a filter with a low strength cannot be used.

In the configuration described in Patent Document 2, the cylindrical member holding the filter is fitted externally and slidably on the container. The cylindrical member is accordingly of a comparatively large size. Therefore, there is space for improvement in terms of reducing the size of the entire sample collection implement.

In the configuration described in Patent Document 3, when the liquid (feces suspension) is filtered, a centrifugal apparatus should be used. Therefore, a centrifugal apparatus should be prepared for the analysis, thereby placing a significant burden on the party involved.

Patent Document 1: Japanese Patent Application Publication No. 2005-114654
Patent Document 2: Japanese Patent No. 3718017
Patent Document 3: Japanese Patent Application Publication No. 2007-170979

DISCLOSURE OF THE INVENTION

It is an object of the present invention to provide a sample collection implement that can adequately prevent or eliminate the above-described inconveniences.

The present invention employs the following technical means for resolving the above-described problems.

A sample collection implement provided by the present invention includes a container having an accommodation portion in which a liquid for suspending or diluting a sample is accommodated, a sample collection stick being able to be disposed in the accommodation portion, and a filter provided inside the container, the sample collection implement further comprising a movable member that can be moved in a predetermined direction inside the container and has a function of pushing the liquid and causing the liquid to pass through the filter, when moved in the predetermined direction.

It is preferred that the movable member be provided separately from the filter and can be moved by being pushed from outside the container.

It is preferred that adjacent first and second regions partitioned by a partition wall be formed inside the container; the filter be disposed in the first region, and when the liquid passes through the filter by the movement of the movable member, at least part of the liquid that has passed through the filter flow into the second region over the partition wall, and be retained in the second region.

It is preferred that the movable member be slidably inserted into the second region and can move down when pushed from above to push the liquid so as to cause the liquid to pass through the filter, and when the liquid that has passed through the filter flows into the second region, the liquid can be retained on the movable member.

It is preferred that the movable member be provided in a location different from the second region; the second region have a form such that a bottom portion thereof is closed by part of the container or by a fixing member separate from the container, and when the liquid that has passed through the filter flows into the second region, the liquid can be retained on the bottom portion.

It is preferred that linking means be further provided that is capable of linking the sample collection stick to the movable member in a state in which the sample collection stick is inserted into the container; the filter be held by the movable member, and the movable member can be moved in the predetermined direction by operating the sample collection stick in a state in which the sample collection stick is linked to the movable member by the linking means.

It is preferred that the linking means include a pair of threaded portions provided at the movable member and the sample collection stick, and an advance operation of the sample collection stick towards the movable member and a rotation operation thereof can be performed in a state in which the sample collection stick is inserted into the container, and the pair of threaded portions can be screwed together by the operations.

It is preferred that the linking means include a concave portion provided in one of the movable member and the sample collection stick, and a convex portion that is provided in the other of the two and can be inserted into the concave portion when the sample collection stick is advanced towards the movable member; the concave portion have a constriction portion that is locally reduced in width, and the convex portion have a protruding portion that engages with the constriction portion to prevent the convex portion from slipping out of the concave portion after the convex portion is inserted into the concave portion.

It is preferred that the sample collection implement in accordance with the present invention further include a power generating element that is disposed inside the container and serves to generate a force that causes the movable member to move in the predetermined direction, and the power generating element can be actuated by a predetermined operation or action outside the container or by the operation of the sample collection stick.

It is preferred that the power generating element be a magnet or a non-magnetized ferromagnetic material constituting at least part of the movable member, and the movable member can be moved in the predetermined direction by causing a magnetic force to act upon the magnet or the ferromagnetic material from the outside of the container or from the sample collection stick.

It is preferred that the movable member be provided so as to form a space partitioned from the accommodation portion inside the container, and the power generating element be a substance for gas generation that is accommodated in the space and the movable member can be moved in the predetermined direction by a gas pressure created when the substance for gas generation generates gas.

It is preferred that the movable member can be engaged with the sample collection stick; an operation causing at least one action from among rotation and movement can be performed with respect to the sample collection stick in a state in which the sample collection stick is inserted into the container, and when the operation is performed and the sample collection stick acts, the movable member moves in the predetermined direction in conjunction with this action.

It is preferred that an outer circumferential surface of the movable member and an inner circumferential surface of the container be provided with a pair of threaded portions that are screwed together; when the sample collection stick is inserted into the container, the sample collection stick assume a state in which the sample collection stick is inserted into a through hole provided in the movable member, can move in the predetermined direction relative to the movable member, and is blocked from rotating relative to the movable member, and when the sample collection stick is rotated, the movable member can be moved in the predetermined direction by a screw feed action of the pair of threaded portions.

It is preferred that the sample collection stick be inserted into a through hole provided in the movable member when the sample collection stick is inserted into the container, and when the sample collection stick is advanced in the direction of insertion into the container by a distance equal to or longer than a predetermined distance, the movable member and the sample collection stick be engaged with each other and the movable member advances in conjunction with the sample collection stick.

Other features and advantages of the present invention will be made more apparent from the description of preferred embodiments thereof illustrated by the appended drawings.

BRIEF DESCRIPTION OF THE DRAWINGS

FIGS. 4A and 4B are cross-sectional views illustrating the usage state of the sample collection implement shown in FIG. 1.

FIG. 5A is a cross-sectional view illustrating another example of the sample collection implement in accordance with the present invention, and FIG. 5B is a cross-sectional view illustrating the usage state thereof.

FIG. 6A is a cross-sectional view illustrating another example of the sample collection implement in accordance with the present invention, and FIG. 6B is a cross-sectional view illustrating the usage state thereof.

FIG. 10A is a plan view of the movable member provided in the sample collection implement shown in FIG. 9, and FIG. 10B is an XB-XB sectional view of the configuration shown in FIG. 10A.

FIGS. 11A and 11B are cross-sectional views illustrating the usage state of the sample collection implement shown in FIG. 9.

FIG. 13A is a cross-sectional view illustrating another example of a sample collection implement in accordance with the present invention, and FIG. 13B is a cross-sectional view illustrating the usage state thereof.

FIGS. 18A and 18B are cross-sectional views illustrating the usage state of the sample collection implement shown in FIG. 17.

FIG. 24A is a cross-sectional view illustrating another example of a sample collection implement in accordance with the present invention, and FIG. 24B is a cross-sectional view illustrating the usage state thereof.

BEST MODE FOR CARRYING OUT THE INVENTION

Figure 1:
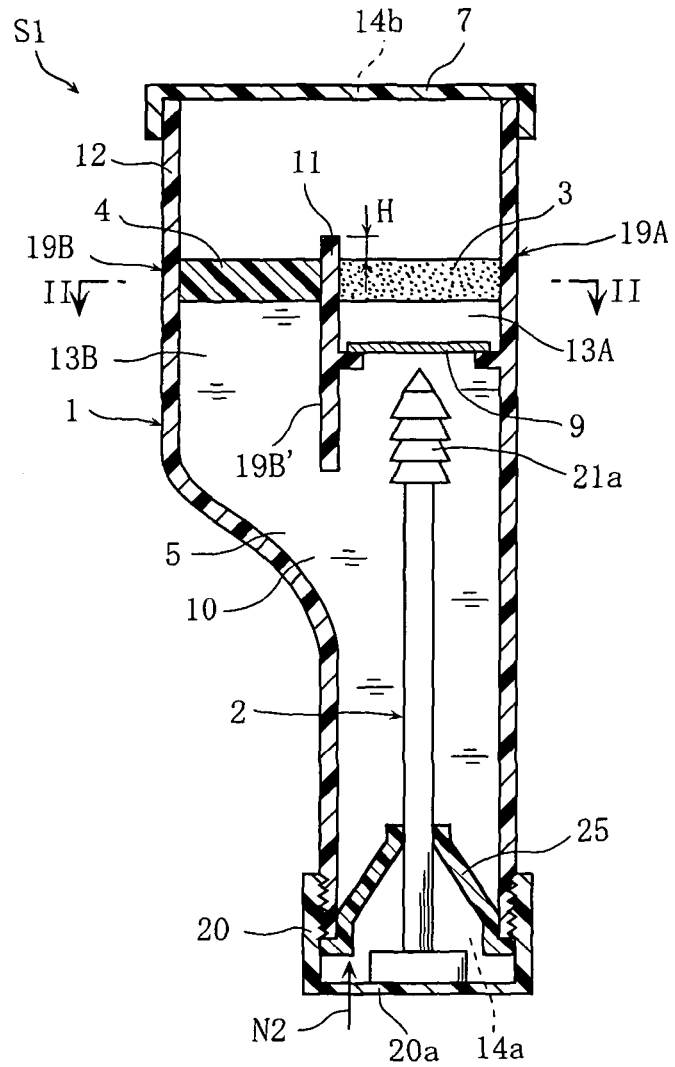
FIG. 1 is a cross-sectional view illustrating an example of a sample collection implement in accordance with the present invention.

The preferred embodiments of the present invention will be described below in greater details with reference to the appended drawings.

There are first to fourth representative types of the sample collection implement in accordance with the present invention. These types will be successively explained below.

[Sample Collection Implement of the First Type]

The sample collection implement of the first type is provided with a movable member that is separate from a filter. Where the movable member is pushed from the outside of a container and moves, a predetermined liquid is filtered by the filter.

FIGS. 1 to 4 illustrate an example of such a sample collection implement of the first type. In the explanation below, the directions such as an up-down direction and a horizontal direction are represented in the drawings. As clearly shown in FIG. 1, the sample collection implement S1 of the present embodiment is provided with a container 1, a sample collection stick 2, a filter 3, and a movable member 4.

Figure 2:
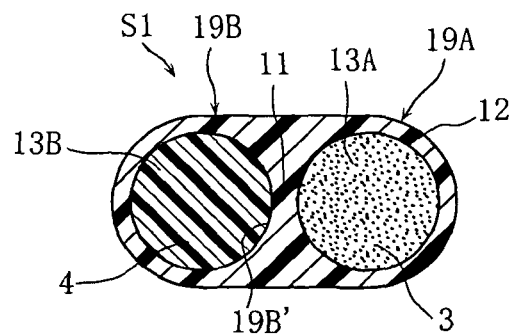
FIG. 2 is a II-II sectional view of the configuration shown in FIG. 1.

The container 1 is made from a synthetic resin and has formed inside thereof an accommodation portion 10 that accommodates a liquid 5 for suspending or diluting a sample. The liquid 5 is, for example, sterilized distilled water or physiological salt solution. A partition wall 11 extending in the up-down direction is provided in a position close to the top portion inside the container 1, and the adjacent first and second regions 13A, 13B are compartmentalized by the partition wall 11. As shown in FIG. 2, the partition wall 11 is linked to a circumferential wall portion 12 of the container 1, and these partition wall 11 and circumferential wall portion 12 constitute two cylindrical potions 19A, 19B defining the first and second regions 13A, 13B, respectively. The filter 3 is arranged in the first region 13A. The movable member 4 is arranged in the second region 13B.

The filter 3 serves to remove components that are unnecessary for analyzing the sample and is fixedly attached to a position close to the upper portion of the first region 13A. For example, when the sample is feces and a fecal occult blood test or a cancer cell test is conducted, the filter 3 serves to remove undigested matter or solid matter such as fiber substances contained in the feces. Specific examples of the filter 3 include a porous body, filtration paper, artificial sponge, degreased cotton, woven fabric, unwoven fabric, a paper filter, a plastic filter, glass fibers, sea sponge, a sintered molding, or a fine gold mesh. Specific examples of the porous body include bodies formed from synthetic resins such as polyethylene and polypropylene. The average pore diameter of the filter 3 is not limited and is for example, 1 to 1000 μm. A shield material 9 is disposed below the filter 3, and the liquid 5 is normally prevented from advancing towards the filter 3. The shield material 9 is for example an aluminum laminated sheet.

A proximal end portion of the sample collection stick 2 is supported by a lid 20 that is screwed onto the lower portion of the container 1. The outer circumferential surface of the distal end portion of the sample collection stick 2 and the peripheral portion thereof are a sample collection portion 21a formed to have a convex-concave outer circumferential surface. The sample collection stick 2 can be inserted into the container 1 from a lower opening 14a of the container 1. In the inserted state of the sample collection stick, the lower opening 14a is closed by the lid 20. In addition, in the inserted state, the distal end of the sample collection stick 2 is disposed close to the lower side of the shield material 9. In the lid 20, a joining portion 20a that is joined to the sample collection stick 2 can be deflected in the up-down direction under the effect of an elastic restoration force. Where the joining portion 20a is pushed upward, as shown by arrow N2, a portion of the shield material 9 can be pierced by the distal end portion of the sample collection stick 2, as shown in FIG. 4A. An extra sample disposal member 25 is provided in the lower portion inside the container 1. The extra sample disposal member 25 serves to dispose of the extra sample that adheres to the sample collection portion 21a when the sample collection stick 2 is inserted into the container 1.

Figure 3A:
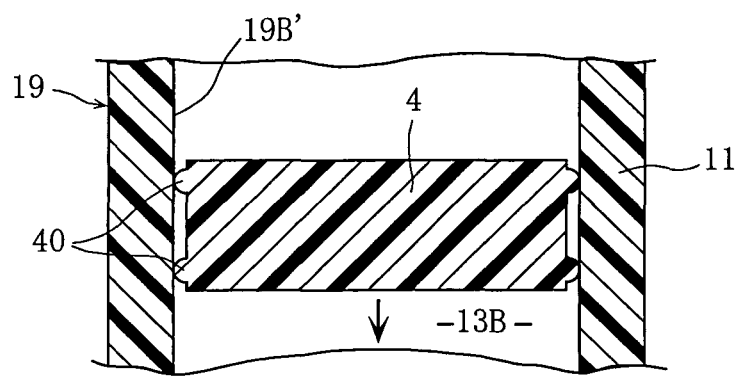
FIGS. 3A and 3B are principal cross-sectional views illustrating specific examples of a detailed structure of a movable member provided in the sample collection implement shown in FIG. 1.
Figure 3B:
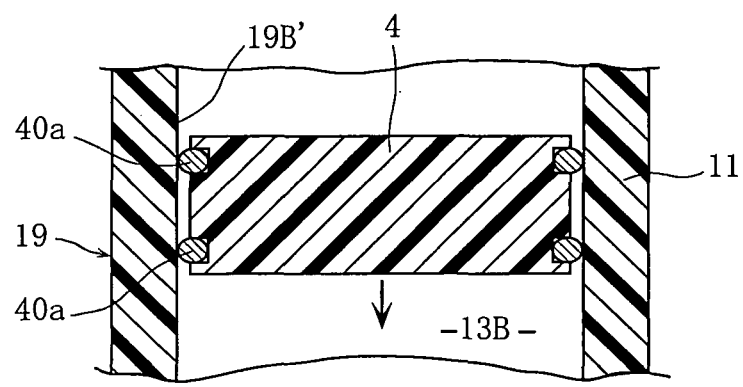

The movable member 4 serves as a piston that applies pressure to the liquid 5 and is made from a comparatively hard synthetic resin. The movable member 4 is disposed close to the upper portion of the second region 13B and descends along an inner circumferential surface 19B' of the cylindrical portion 19B when a pressure is applied to the movable member downward from above by a force equal to or higher than a predetermined force. FIG. 1 and FIG. 4 represent the form of the movable member 4 in a simplified manner, but the movable member 4 is preferably configured, for example, as shown in FIG. 3A or FIG. 3B. In the configuration shown in FIG. 3A, a plurality of protruding portions 40 are formed on the outer circumferential surface of the movable member 4. When the movable member 4 descends, the plurality of protruding portions 40 slide in contact with the inner circumferential surface 19B' of the cylindrical portion 19B, thereby demonstrating a sealing function. It is even more preferable that the protruding portions 40 be elastically deformable. In the configuration shown in FIG. 3B, a plurality of O-rings 40a composed of an elastic material are fitted and mounted on the outer circumferential surface of the movable member 4. When the movable member 4 descends, the plurality of O-rings 40a slide in contact with the inner circumferential surface 19B', thereby demonstrating a sealing function. The configurations shown in FIG. 3A or 3B can be also applied to movable members 4A to 4M of the below-described other embodiments.

An opening 14b that is closed by a lid 7 is formed in the upper portion of the container 1, and the upper side of the movable member 4 is open when the lid 7 is removed. Accordingly, as shown in FIGS. 4A and 4B, a suction nozzle 8 of an automatic analyzer (not shown in the figure) can be lowered from above the container 1 to apply pressure to the movable member 4.

Where the movable member 4 descends, a pressure is applied to the liquid 5 in the accommodation portion 10. Therefore, as shown in FIG. 4B, where the shield material 9 has been ruptured in advance, part of the liquid 5 passes upward through the filter 3. The height H from the upper surface of the filter 3 to the upper end of the partition wall 11 is comparatively small. Where the filtered amount of the liquid 5 becomes equal to or greater than a predetermined amount, the liquid 5' that has passed through the filter 3 flows over the upper end of the partition wall 11, as shown by arrow N1 in FIG. 4B, flows onto the movable member 4 and stays on the movable member 4.

The operation of the sample collection implement S1 will be explained below.

When feces are collected as a sample, the sample collection stick 2 is pulled out of the container 1, and a sample (not shown in the figure) is caused to adhere to the sample collection portion 21a. The sample collection stick 2 is then inserted into the container 1 to assume an original position. As a result, part of the sample that has adhered to the sample collection portion 21a diffuses into the liquid 5 and the liquid 5 becomes a suspension. For example, a configuration can be used in which the sample collection stick 2 is shaken in the horizontal direction after being inserted into the container 1 as a means for enhancing the diffusion of the sample.

Then, where a fecal occult blood test or a cancer cell test is conducted, part of the shield material 9 is ruptured by using the sample collection stick 2, as has been explained with reference to FIG. 4A. The lid 7 is then removed from the container 1. In such a state, the sample collection implement S1 is set to a predetermined position in an automatic analyzer (not shown in the figure). In the course of analysis, the suction nozzle 8 of the analyzer that can be moved in the vertical direction is used to apply a pressure to the movable member 4 and move the movable member down as shown in FIG. 4B. As a result of this operation, as has already been explained above, the liquid 5 (sample suspension) passes upward through the filter 3. Where the amount of liquid 5' that has been filtered by the filter 3 becomes equal to or greater than a predetermine amount, the liquid 5' flows over the upper portion of the partition wall 11 onto the movable member 4 and stays thereon. Therefore, the liquid 5' can be directly sucked in by the suction nozzle 8 and taken into the automatic analyzer.

As mentioned hereinabove, in the sample collection implement S1, it is not necessary to apply a pressure to the filter 3 by the nozzle 8, and the filter 3 remains in a fixed state. The resultant advantage is that a material with a comparatively low mechanical strength can be used as the filter 3. Meanwhile, since a configuration may be used in which when a pressure is applied by the suction nozzle 8 to the movable member 4, the movable member moves down so as to push the liquid 5 in the second region 13B. Therefore, the structure of the movable member can be simplified. In addition, the movable member 4 can be formed in a small size. As a consequence, the sample collection implement S1 can be advantageously reduced in size and production cost. Furthermore, in the sample collection implement S1, the liquid 5' that has passed through the filter 3 flows onto the movable member 4 and can be directly sucked by the suction nozzle 8 that pushes and lowers the movable member 4. Therefore, no special means for pushing the movable member 4 has to be separately provided, and a more rational configuration of the sample collection implement is obtained.

FIGS. 5A to 8B illustrate another example of the sample collection implement of the first type. In these figures, elements identical or analogous to those in the above-described embodiment are assigned with same reference numerals as in the above-described embodiment. The same is true for the below-described FIGS. 9 to 24B, and the explanation of features identical to those of the earlier described embodiments will be omitted.

In a sample collection implement S2 shown in FIG. 5A, a cylindrical portion 70 having a filter 3A inserted therein and fixed thereto is provided in the upper portion inside a container 1A. The cylindrical portion 70 is provided, for example, in a lid 7A mounted on the upper portion of the container 1A. A seal material 9 is provided in the lower portion of the cylindrical portion 70. A movable member 4A formed in a ring-like shape is slidably inserted into a space portion 15 formed between the cylindrical portion 70 and a circumferential wall portion 12 of the container 1A. A plurality of holes 71 are provided to pass through the lid 7A in the up-down direction above the movable member 4A. A cover sheet 79 that closes the plurality of holes 71 and an upper opening of the cylindrical portion 70 is adhesively bonded to the upper surface of the lid 7A to prevent dust or the like from penetrating into the container 1A.

When the sample collection implement S2 is set in an automatic analyzer, the sample that has been collected in advance by using the sample collection stick 2 is caused to diffuse into the liquid 5. Further, as shown in FIG. 5B, the shield material 9 is ruptured by using the sample collection stick 2. In such a state, the suction nozzle 8 and a pusher 80 provided separately therefrom are lowered from above the container 1A into the cylindrical portion 70 and the space portion 15. In this case, the cover sheet 79 is pierced by the suction nozzle 8 and the pusher 80. The, movable member 4A is then pushed by the pusher 80 and lowered. As a result, the liquid 5 penetrates upward through the filter 3A, and the liquid 5' that has been filtered by the filter 3A can be sucked in by the suction nozzle 8 and taken into the automatic analyzer.

In the present embodiment, although the pusher 80 has to be provided in the automatic analyzer as a means for pushing down and lowering the movable member 4A, the pusher 80 can simply perform the lifting-lowering operation. Therefore, a simple mechanism can be used for operating the pusher 80. Further, in the present embodiment, the movable member 4A has a ring-like shape and the movable member 4A moves at a circumference of an attachment location of the filter 3A. Therefore, the movable member 4A and the filter 3A can be efficiently disposed in a space-saving manner inside the container 1A and the increase in size of the container 1A is inhibited. The upper region where the movable member 4A and the filter 3A are provided and the lower region where the sample collection stick 2 is mounted, in the container 1A, can be easily made to have substantially the same diameter and the entire sample collection implement S2 can be made slimmer.

In a sample collection implement S3 shown in FIG. 6A, first and second regions 13A, 13B partitioned by a partition wall 11 are compartmentalized and formed in the upper portion inside a container 1B. The lower portion of the second region 13B has no opening and is closed by a bottom portion 17 formed by part of the container 1B. A reagent R for sample analysis is provided in the bottom portion 17. A cylindrical portion 16 linked by the inside thereof to an accommodation portion 10 of a liquid 5 is provided in a position in the container 1B such that interference with the sample collection stick 2 can be avoided, and a movable member 4B is inserted into the cylindrical portion 16 so that the movable member can slide in the vertical direction.

When the sample collection implement S3 is set in an automatic analyzer, the sample that has been collected in advance by using the sample collection stick 2 is caused to diffuse into the liquid 5 and then, as shown in FIG. 6B, a shield material 9 is ruptured by using the sample collection stick 2. A lid 7 is also removed. Where the movable member 4B is pushed and lifted by a pusher 81 in this state, the liquid 5 passes through a filter 3B and the liquid 5' that has been filtered by the filter 3B flows over the partition wall 11 and into the second region 13B and remains on the bottom portion 17. As a result, the reagent R and the liquid 5' react in the second region 13B and the reaction liquid 5'' thereof is produced.

Where the reaction liquid 5″ is produced, analysis of the sample can be performed by disposing an optical analyzer (not shown in the figure) for examining the reaction liquid 5″, for example, by colorimetry above the container 1B. Thus, in the sample collection implement S3, the second region 13B functions as a reaction chamber for the liquid 5′ and the reagent R, and the liquid 5′ can be rapidly analyzed without being taken to the outside of the sample collection implement S3. It goes without saying that in accordance with the present invention a configuration in which the reagent R is not provided in advance in the second region 13B can be also used, this configuration being different from that described above. In this case, a reagent is charged at a later stage into the second region 13B, the second region 13B is caused to function as a reaction chamber, and a technique of analyzing the sample can be used. Further, a technique can be also used by which a test piece is immersed in the liquid 5′ remaining in the second region 13B and the sample is analyzed; in this case the second region 13B can be caused to function as a measurement unit for the liquid 5′. In addition, it is also possible to take the liquid 5′ from the second region 13B into an analytical processing device.

Figure 7:
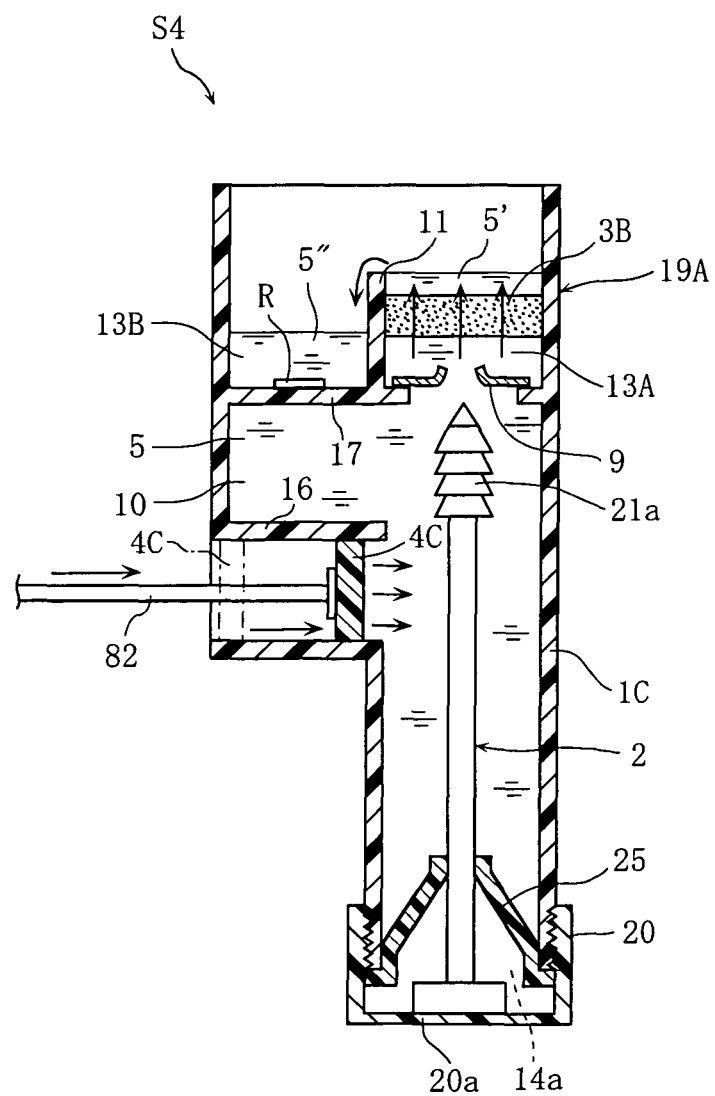
FIG. 7 is a cross-sectional view illustrating another example of a sample collection implement in accordance with the present invention.

A sample collection implement S4 shown in FIG. 7 shares the basic configuration with the above-described sample collection implement S3. However, the cylindrical portion 16 formed in a container 1C extends almost horizontally and a movable member 4C is inserted into the cylindrical portion 16 so that the movable member can slide in a substantially horizontal direction. In the sample collection implement S4, where the movable member 4C is pushed and moved by a pusher 82 in a substantially horizontal direction, part of the liquid 5 passes upward through a filter 3B and the operation that is generally similar to that of the above-described sample collection implement S3 is obtained. As follows from this embodiment and the above-described other embodiments, in accordance with the present invention, no limitation is placed on the direction in which the movable member is pushed.

Figure 8A:
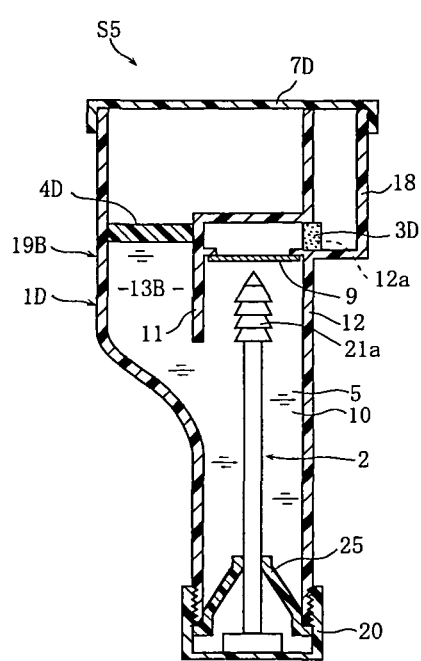
FIG. 8A is a cross-sectional view illustrating another example of the sample collection implement in accordance with the present invention.

In a sample collection implement S5 shown in FIG. 8A, a movable member 4D is disposed close to the upper portion of a second region 13B. A filter 3D is inserted in and fixed to a hole 12a provided in a circumferential wall portion 12 of the container 1D. An auxiliary portion 18 with an open top is formed in the upper portion of the container 1D for retaining the liquid 5′ that has passed through the filter 3D.

Figure 8B:
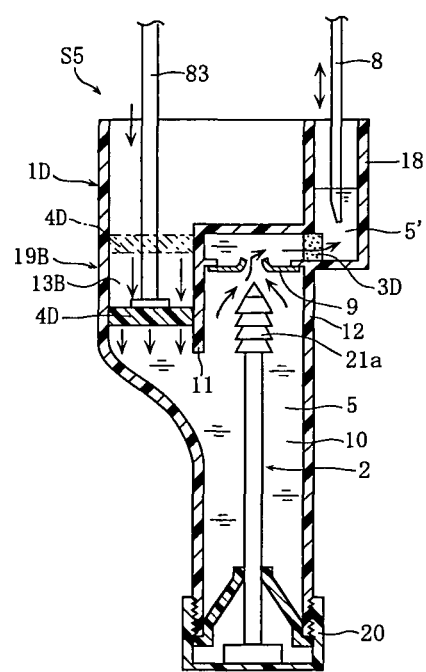
FIG. 8B is a cross-sectional view illustrating the usage state thereof.

When the sample collection implement S5 is set in an automatic analyzer, a lid 7D located on the top of the container 1D is removed and a shield material 9 is ruptured, as shown in FIG. 8B. Where a movable member 4D is pushed and lowered by a pusher 83 in this state, part of the liquid 5 passes through the filter 3D in a substantially horizontal direction, and the liquid 5′ that has been filtered by the filter 3D is retained in the auxiliary portion 18. This liquid 5′ can be sucked in by a suction nozzle 8 inserted from above the auxiliary portion 18. As follows from this embodiment and the above-described other embodiments, in accordance with the present invention, a direction in which the liquid passes through the filter is not particularly limited and can be also a substantially horizontal direction, instead of the upward direction.

[Sample Collection Implement of the Second Type]

The sample collection implement of the second type is provided with a movable member that holds a filter. The movable member can be linked to a sample collection stick, and the movable member and the filter can be moved according to the operation of the sample collection stick, thereby performing filtration of a predetermined liquid by using the filter.

FIGS. 9 to 11B illustrate an example of the sample collection implement of the second type. As clearly shown in FIG. 9, in a sample collection implement S6 of the present embodiment, a movable member 4E is inserted into the upper portion inside a substantially cylindrical container 1E so that the movable member can slide in the up-down direction. A filter 3E is supported by the movable member 4E. The movable member 4E and a sample collection stick 2E can be linked together by using threaded portions 41a, 21b.

More specifically, as shown in FIGS. 10A and 10B, a threaded hole 41 that is open downward and has a threaded portion 41a and a ring-shaped concave portion 42 that is open downward and positioned around the threaded hole 41 are formed in the movable member 4E. The filter 3E has a ring-like shape and is inserted and held in the concave portion 42. A shield material 9 is provided in the lower portion of the movable member 4E, and in the normal state, the liquid 5 is prevented from moving towards the filter 3E. A plurality of openings 43 are provided in the upper portion of the movable member 4E.

Figure 9:
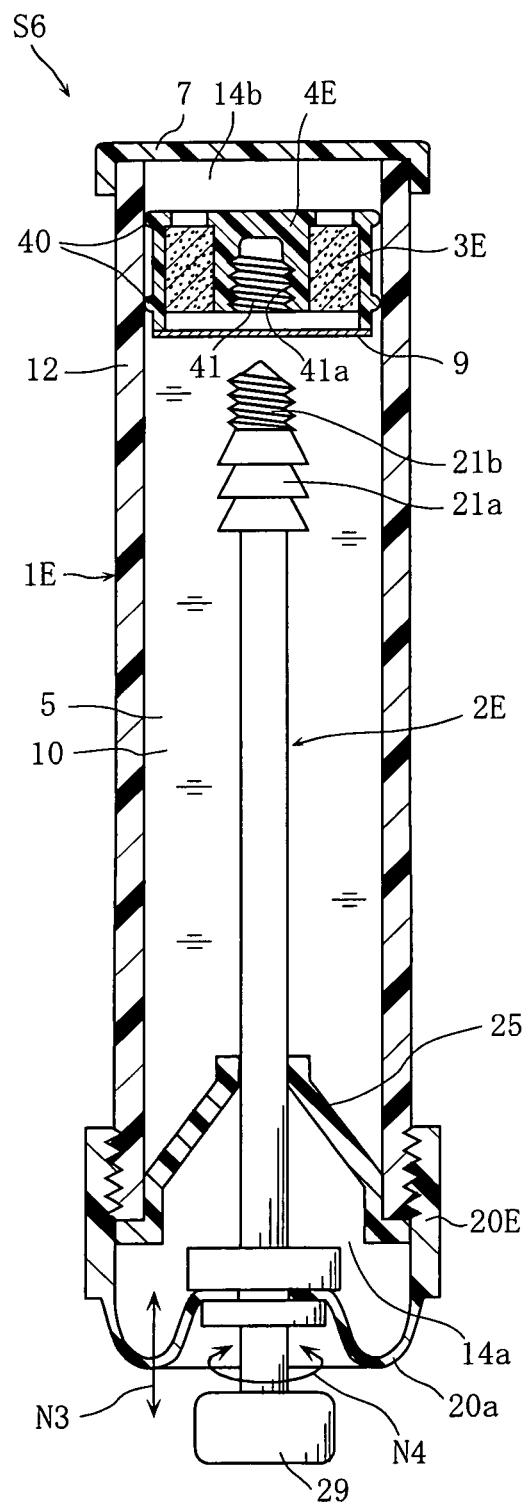
FIG. 9 is a cross-sectional view illustrating another example of a sample collection implement in accordance with the present invention.

As shown in FIG. 9, a threaded portion 21b is provided in the distal end portion of the sample collection stick 2E. An operation knob 29 positioned below a lid body 20E is provided at the proximal end of the sample collection stick 2E. In the lid body 20E, a linking portion 20a that is linked to the sample collection stick 2E has comparatively high flexibility in the up-down direction, and the sample collection stick 2E can be moved in the up-down direction shown by an arrow N3 by gripping and operating the knob 29. In addition, the sample collection stick 2E can be rotated relative to the linking portion 20a, and can be rotated in the direction shown by an arrow N4 by gripping and operating the knob 29. Therefore, in the sample collection stick S6, as shown in FIG. 11A, after the shield material 9 has been ruptured by raising the sample collection stick 2E, the sample collection stick 2E can be further raised and rotated, thereby screwing the threaded 21b into the threaded portion 41a and linking the sample collection stick 2E to the movable member 4E. The combination of the threaded portions 21b, 41a corresponds to an example of the linking means in accordance with the present invention.

In order to examine the sample after the sample has been caused to diffuse into the liquid 5, first, as has been explained with reference to FIG. 11A, the threaded portions 21b, 41a are screwed together to link the sample collection stick 2E and the movable member 4E. Then, as shown in FIG. 11B, the knob 29 is gripped and the sample collection stick 2E is lowered. As a result, the movable member 4E is also lowered and part of the liquid 5 passes upward through the filter 3E. The liquid 5′ that has thus been filtered is retained on the movable member 4E and sucked in, for example, by using the suction nozzle 8 of the automatic analyzer.

Thus, in the present embodiment the movable member 4E holding the filter 3E is lowered by using the sample collection stick 2E. Therefore, it is not necessary to apply a pressure directly to the filter 3E. As a result, the filter 3E can be prevented from damage. Further, since it is not necessary to provide the sample collection implement S6 with a special part for lowering the movable member 4E, separately from the sample collection stick 2E, the increase in the number of parts in the entire device can be inhibited, the entire configuration can be simplified and the size thereof can be reduced. Further, since the movable member 4E and the sample collection stick 2E are linked by screwing together the pair of threaded portions 21b, 41a, these movable member 4E and sample collection stick 2E can be linked strongly and reliably.

Therefore, even when friction resistance is comparatively high when the movable member 4E is lowered, the movable member 4E can be adequately lowered together with the filter 3E.

Figure 12A:
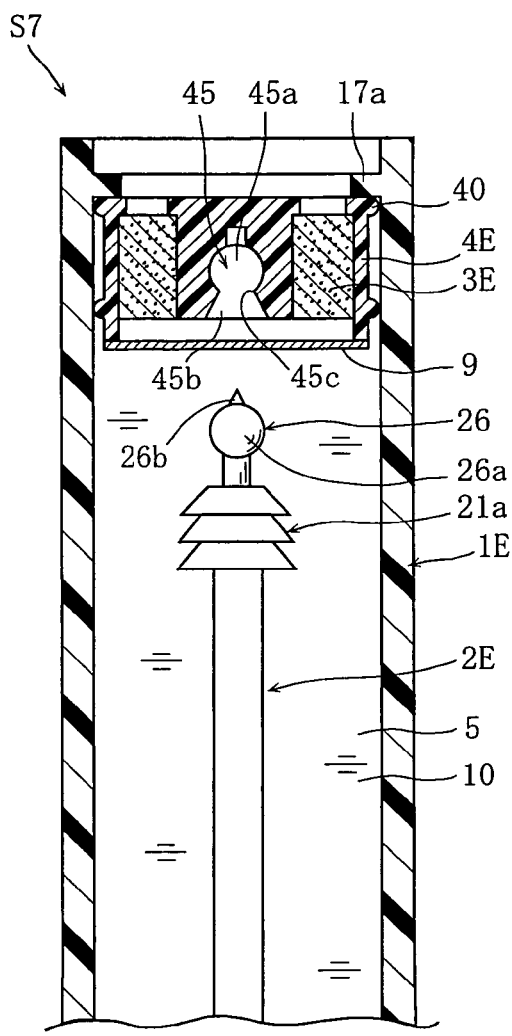
FIG. 12A is a principal cross-sectional view illustrating another example of a sample collection implement in accordance with the present invention.
Figure 12B:
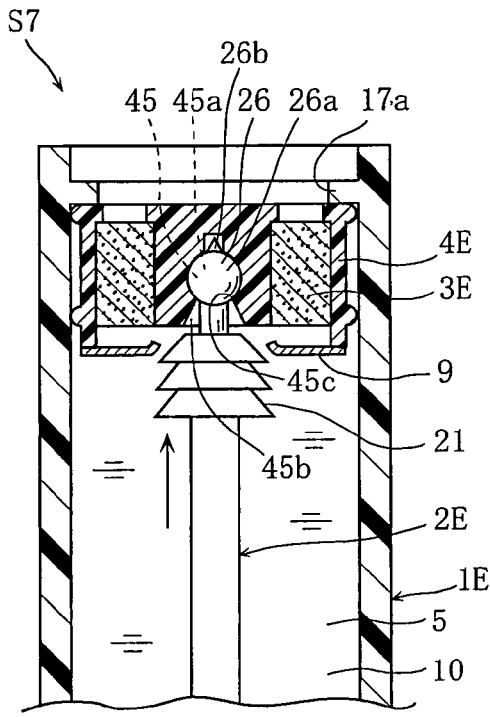
FIGS. 12B and 12C are principal cross-sectional views illustrating the usage state thereof.
Figure 12C:
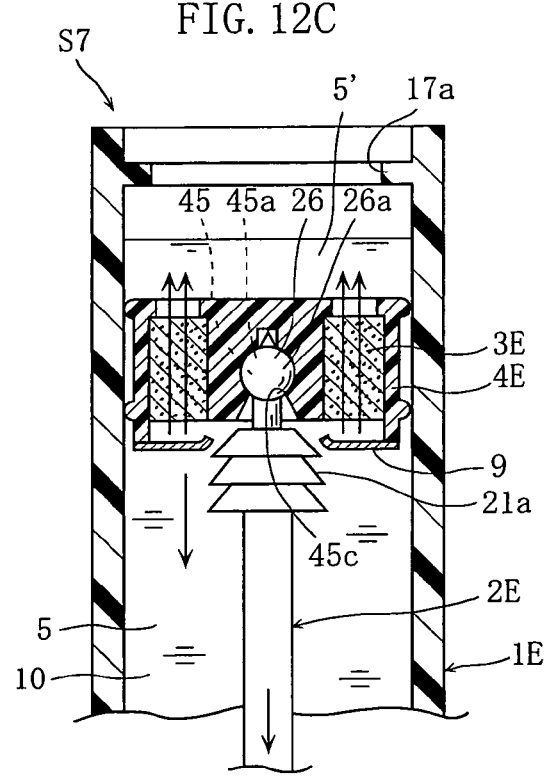

FIGS. 12A to 12C illustrate another example of the sample collection implement of the second type.

As shown in FIG. 12A, in a sample collection implement S7 of the present embodiment, a structure in which a concave portion 45 that is open at a lower end and formed in a movable member 4E is combined with a convex portion 26 formed at the distal end portion of a sample collection stick 2E is used as a means for linking the movable member 4E and the sample collection stick 2E. The concave portion 45 has a configuration in which an auxiliary cavity 45b in the form of a truncated cone is coupled with a lower side of a main cavity 45a of a substantially spherical shape, and a boundary portion of the main cavity 45a and the auxiliary cavity 45b serves as a constriction portion 45c. The convex portion 26 has a sharp distal end portion 26b for piercing a shield material 9 and a substantially spherical protruding portion 26a. The diameter of the protruding portion 26a is larger than the inner diameter of the constriction portion 45c. When the protruding portion 26a is moved forward into the concave portion 45 and strongly pressed against the constriction portion 45c, the constriction portion 45c is elastically deformed and the protruding portion 26a can be inserted into the main cavity 45a. In such an inserted state, the protruding portion 26a is engaged with the constriction portion 45c so that the protruding portion cannot be easily released downward of the main cavity 45a. A stopper convex portion 17a that prevents the movable member 4E from rising when the convex portion 26 is inserted into the concave portion 45 is provided in the upper portion of the container 1E.

In the sample collection implement S7, after the sample collection stick 2E has been raised and the shield material 9 has been ruptured, as shown in FIG. 12B, the convex portion 26 can be inserted into the concave portion 45. In a state in which these concave portion 45 and convex portion 26 are joined, the protruding portion 26a and the constriction portion 45c are engaged, the convex portion 26 is prevented from easily falling down from the concave portion 45, and the movable member 4E and the sample collection stick 2E can be reliably linked. Therefore, where the sample collection stick 2E is thereafter lowered as shown in FIG. 12C, the movable member 4E is also lowered and part of the liquid 5 passes through the filter 4E. The filtered liquid 5' is retained on the movable member 4E.

In the present embodiment, when the movable member 4E and the sample collection stick 2E are linked, it is possible only to lift the sample collection stick 2E and, by contrast with the above-described sample collection implement S6, it is not necessary to rotate the sample collection stick 2E. Therefore, in the present embodiment, operability is further improved. Further, since it is not necessary to make the sample collection stick 2E rotatable, the structure of the sample collection implement S7 can be simplified.

In the sample collection implement of the second type such as described above, the linking means for linking the sample collection stick and the movable member is not limited to the above-described configuration using the joining portions or the structure combining the concave portion having the constriction portion and the convex portion having the protruding portion. For example, the sample collection stick and movable member can be also configured by forming a concave portion or a convex portion of a shape different from that of the above-descried concave portion or convex portion and joining the portions so that they can be prevented from separating. The concave portion and convex portion can be prevented by separating, for example, by rotating the sample collection stick through an appropriate angle. Furthermore, a more traditional technique of adhesively bonding and joining when the distal end portion of the sample collection stick is brought into contact with the movable member can be also used.

[Sample Collection Implement of the Third Type]

The sample collection implement of the third type has a configuration in which a movable member and a power generating element are disposed inside a container. The movable member is moved by actuating the power generating element, and the filtration of a predetermined liquid by a filter is performed by the movement of the movable member.

FIGS. 13A and 13B illustrate an example of a sample collection implement of the third type. In a sample collection implement S8 of the present embodiment, a movable member 4F is disposed inside an auxiliary chamber 13 provided in a container 1F. The movable member 4F is provided with a sheet-like magnet 49. The magnet 49 corresponds to an example of a power generating element in accordance with the present invention.

More specifically, a filter 3F held in a holder 30 is fixedly provided in the upper portion inside the container 1F, and a shielding material 9 is provided below the filter 3F. The auxiliary chamber 13 is provided by stretching out part of a circumferential wall portion 12 of the container 1F to the outside of the container 1F, and the auxiliary chamber constitutes part of an accommodation portion 10 where a liquid 5 is accommodated. The movable member 4F has a configuration in which a sheet-like magnet 49 is fixedly attached to one surface of a main body 46 made from a synthetic resin. Therefore, where a magnet MG is disposed in the vicinity of the magnet 49 on the outside of the container 1F, as shown by virtual lines in FIG. 13B, and a repulsion force is generated between these magnets 49 and MG, the movable member 4F can be moved towards the center of the container 1 as shown by an arrow N5. The main body 46 can slide with respect to an inner wall surface 13a of the auxiliary chamber 13, while maintaining sealing ability. Therefore, when the movable member 4F moves in the direction shown by the arrow N5, the liquid 5 is pushed by the main body 46.

In the configuration shown in FIGS. 13A and 13B, the magnet 49 is provided over substantially the entire one surface of the main body 46. However, in accordance with the present invention, the magnet 49 can be instead provided only in a portion of one surface of the main body 46 or can be provided in a dispersed manner in a plurality of places. In a configuration in which only one magnet 49 is provided and the magnet 49 has a pair of magnetic poles, namely, an N pole and a S pole, when a separate magnet is accidentally disposed in the vicinity of the container 1 and this separate magnet is oriented to repulse the magnet 49, the movable member 4F can be moved unintentionally. Therefore, for example, it is possible to use a configuration in which a plurality of magnets 49 are disposed in a dispersed manner and a plurality of combinations of magnetic poles (N poles and S poles) are provided in the movable member 4F, such a configuration preventing the aforementioned inconvenience. With such a configuration, the movable member 4F cannot be moved unintentionally, unless a plurality of magnets corresponding to the plurality of combinations of magnetic poles are disposed in the vicinity of the container 1, and the possibility of the movable member 4F being accidentally moved is reduced.

In the sample collection implement S8 of the present embodiment, similarly to the above-described embodiments, a sample is dispersed in advance in the liquid 5, the sample collection stick 2 is pushed upward as shown by an arrow N6, and the part of the shield material 9 is ruptured. In this state, as described with reference to FIG. 13B, the magnet MG is disposed in the vicinity of the magnet 49 of the movable member 4F and a force of mutual repulsion is generated between the two magnets. Thus, the movable member 4F is moved towards the center of the container 1F and the liquid 5 is pushed by the movable member 4F. As a result, part of the liquid 5 passes through the filter 3F. A liquid 5' that has thus been filtered is retained on the filter 3F and can be taken into an automatic analyzer by using a suction nozzle 8.

Thus, in the sample collection implement S8, similarly to the sample collection implements S1 to S7 of the above-described first and second types, it is not necessary to push the filter 3F with the suction nozzle 8 and the filter 3F remains fixed. Therefore, a filter with a comparatively low mechanical strength can be used as the filter 3F. Since it is suffice to dispose the magnet MG at one side of the container 1 and bring this magnet relatively close to the magnet 49 to perform the operation of moving the movable member 4F, the operation is extremely simple and can be easily automated. An electromagnet can be also used, instead of a permanent magnet, as the magnet MG.

FIGS. 14 to 20 show another example of a sample collection implement of the third type.

Figure 14:
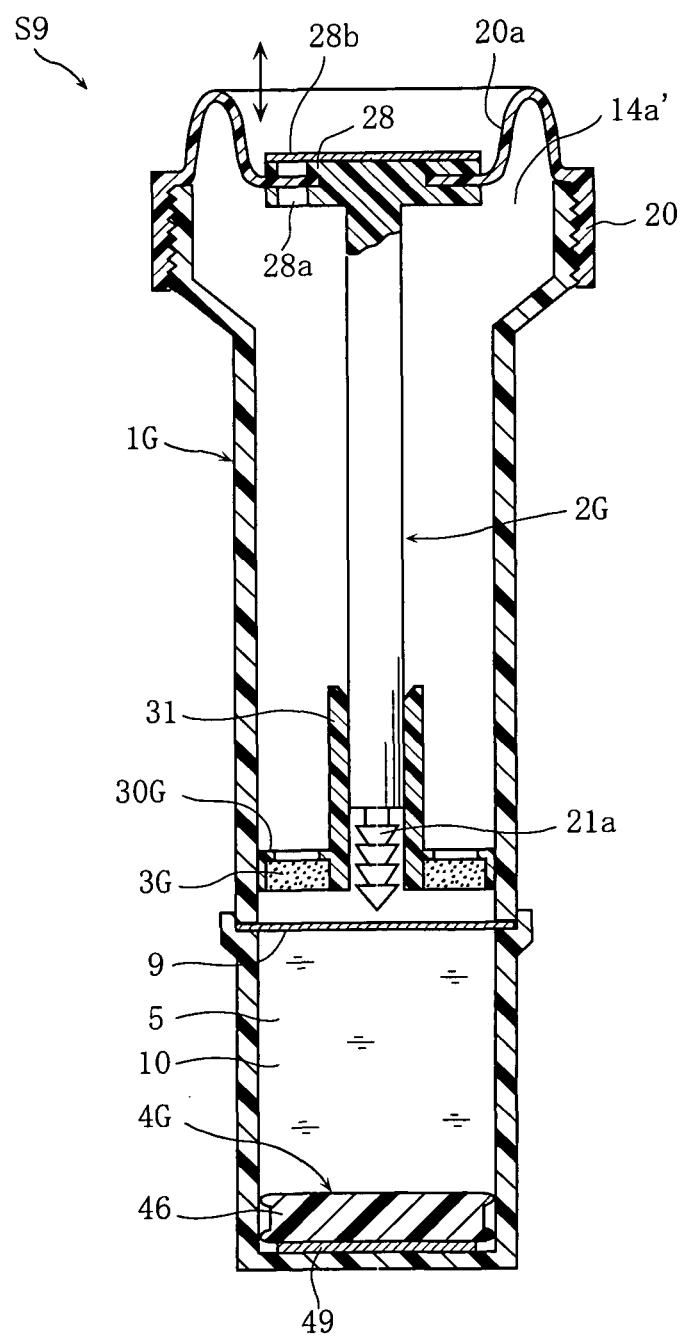
FIG. 14 is a cross-sectional view illustrating another example of a sample collection implement in accordance with the present invention.

In a sample collection implement S9 shown in FIG. 14, a movable member 4G provided with a magnet 49 is slidably inserted in a lower portion of a substantially cylindrical container 1G. A region close to the lower portion inside the container 1G is an accommodation portion 10 that accommodates a liquid 5 and is sealed by a sealing material 9. A ring-shaped filter 3G supported by a holder 30G is fixedly provided above the shielding material 9.

Figure 15A:
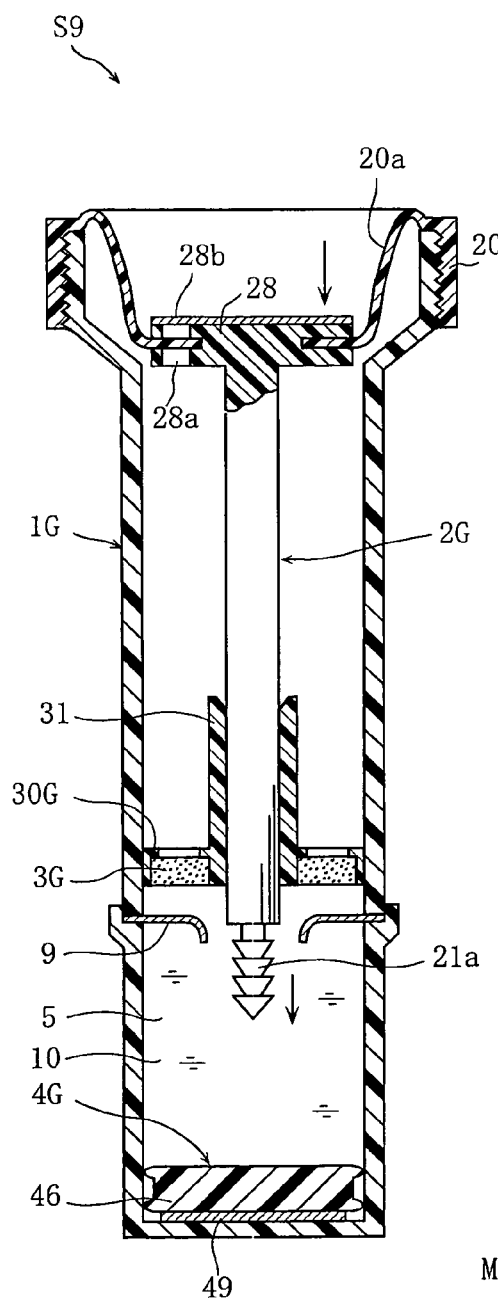
FIGS. 15A and 15B are cross-sectional views illustrating the usage state of the sample collection implement shown in FIG. 14.
Figure 15B:
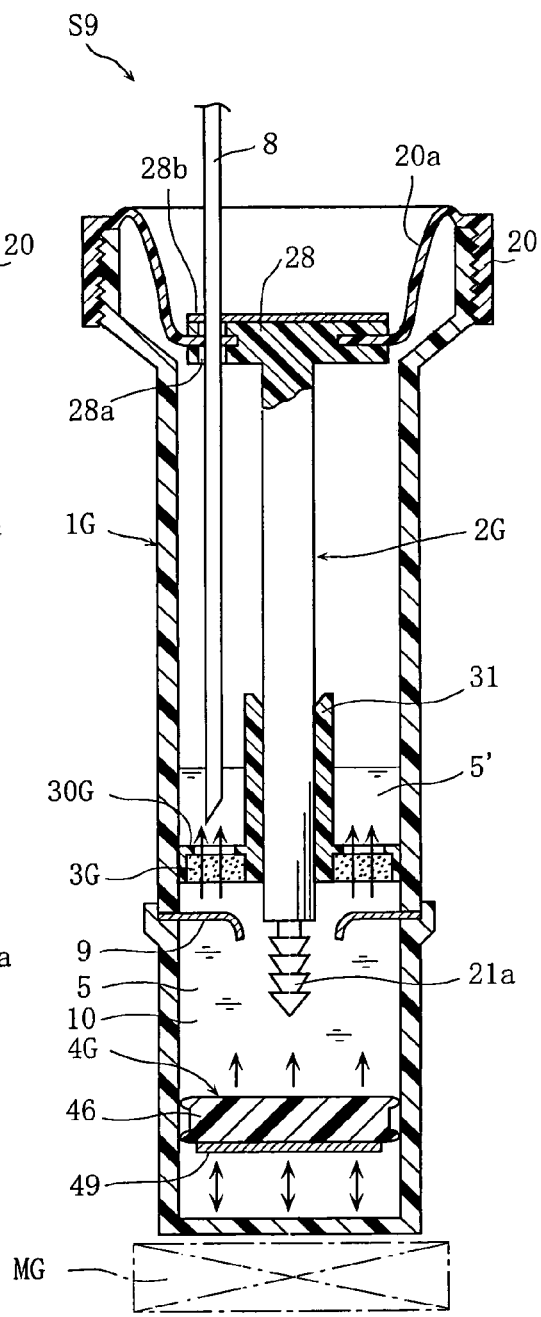

A sample collection stick 2G can be inserted downward into the container 1G from an opening 14a' provided in the upper portion of the container 1G, and the distal end portion of the sample collection stick can be inserted into a cylindrical portion 31 provided at the holder 30G. FIG. 14 illustrates a state in which the sample collection stick 2G has not yet been used for sample collection. In this state, the lower end tip of the sample collection stick 2G is positioned above the shielding material 9, without piercing the shielding material 9. A linking portion 20a of a lid 20 has comparatively large flexibility in the up-down direction and is configured such that the sample collection stick 2G can be lowered with a comparatively large stroke, as shown in FIG. 15A, from the state shown in FIG. 14 and a sample collection portion 21a can be sufficiently dipped into the liquid 5 after the shielding material 9 has been pierced. A hole 28a that is sealed by a cover sheet 28b is provided in a flange portion 28 in the upper portion of the sample collection stick 2G. The hole 28a serves to insert a suction nozzle 8, as shown in FIG. 15B.

When the sample collection implement S9 of the present embodiment is used, first, in a state shown in FIG. 14, the sample collection stick 2G is pulled out of the container 1G and the sample is collected in the sample collection portion 21a. Then, as shown in FIG. 15A, the sample collection stick 2G is inserted into the container 1G. In the insertion process, the sample collection stick 2G is used to pierce the shielding material 9 and the sample collection portion 21a is dipped into the liquid 5. As a result, the sample can be caused to diffuse adequately into the liquid 5. When sample examination is thereafter performed, the magnet MG is disposed in the vicinity of the lower side of the container 1G, as shown in FIG. 15B, and a repulsion force is generated between the magnets 49 and MG. As a result, the movable member 4G is lifted. Therefore, the liquid 5 is pushed up by the movable member 4G and part of the liquid 5 passes upward through the filter 3G. The liquid 5' that has thus been filtered can be sucked in by the suction nozzle 8 and taken into a predetermined automatic analyzer. The suction nozzle 8 can be adequately introduced into the container 1G by piercing the cover sheet 28b and inserting into the hole 28a.

In the present embodiment, the movable member 4G is disposed in the lower portion of the container 1G. Therefore, the movable member 4G can be operated and the liquid 5 can be adequately filtered by using the magnet MG as in the above-described sample collection implement S8. The structures of the sample collection implements S8 and S9 clearly indicate that no limitation is placed on specific orientation and movement direction of the movable member provided with a magnet in the configurations according to the present invention.

Figure 16:
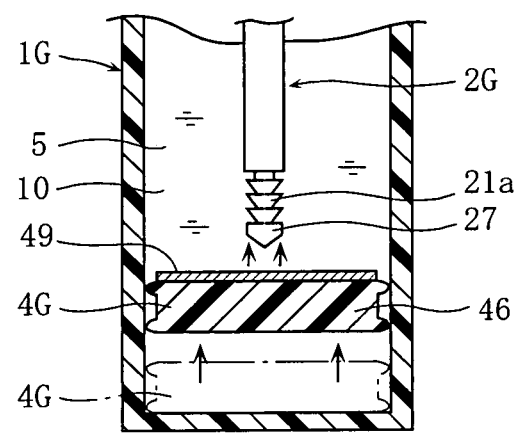
FIG. 16 is a principal cross-sectional view illustrating another example of a sample collection implement in accordance with the present invention.

In the embodiment shown in FIG. 16, the magnet 27 is provided at a distal end of the sample collection stick 2G, this feature being different from those of the above-described sample collection implement S9. In the present embodiment, when the distal end of the sample collection stick 2G is brought close to the movable member 4G, the movable member 4G can be raised by repulsion forces of the magnet 27 and the magnet 49 of the movable member 4G. As follows from the present embodiment, in accordance with the present invention, a means for providing a magnet at the sample collection stick can be used instead of the means for disposing a magnet outside of the container as a means for causing a magnetic force to act upon the movable member.

In the embodiment shown in FIGS. 13A to 16, part of the movable member is taken as a magnet, but the present invention is not limited to this configuration. Thus, the entire movable member can be configured as a magnet. Furthermore, in accordance with the present invention, a non-magnetized ferromagnetic material can be also used instead of the magnet. When the entire movable member or part thereof is from a ferromagnetic material, by disposing a magnet outside of the container it is possible to move the movable member close to the magnet and push the liquid located inside the container. However, when the entire movable member or part thereof is from a ferromagnetic material, when a magnet is accidentally disposed close to the container, the movable member can be attracted to the magnet and moved unintentionally, regardless of the kind of poles of the magnet. Therefore, from the standpoint of reducing the probability of such inconvenience, it is preferred that the entire movable member or part thereof be a magnet.

Figure 17:
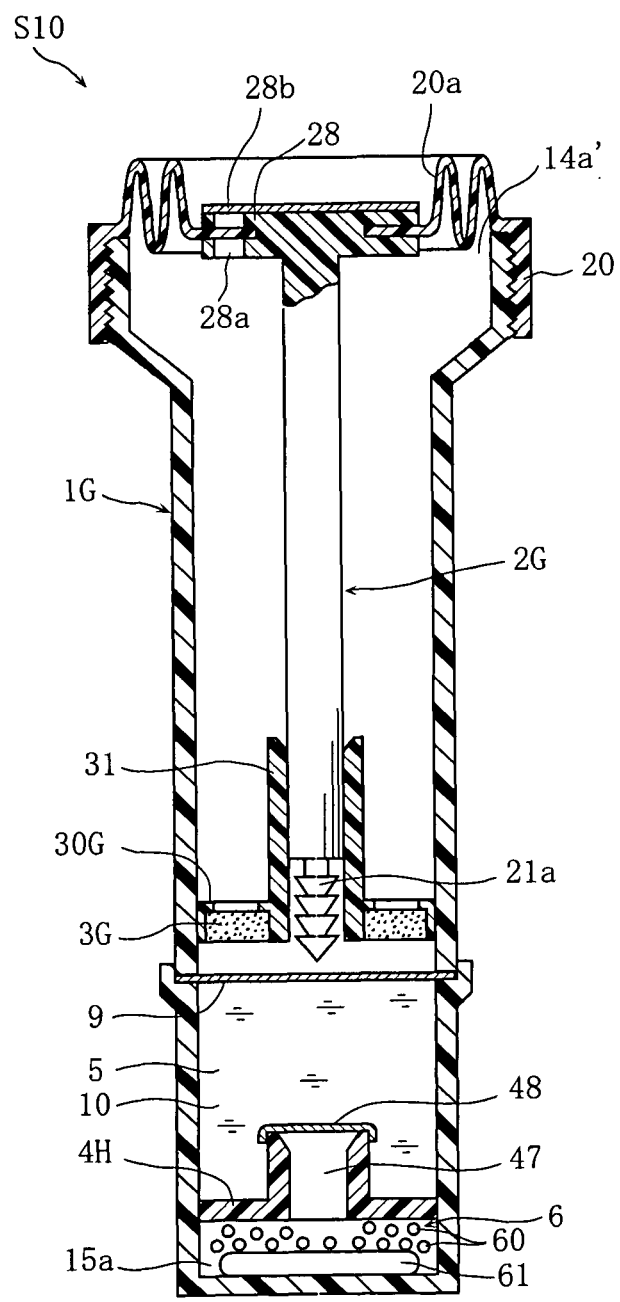
FIG. 17 is a cross-sectional view illustrating another example of a sample collection implement in accordance with the present invention.

In a sample collection implement S10 shown in FIG. 17, a movable member 4H and a means for raising the movable member 4H are different from those of the sample collection implement S9 shown in FIG. 14, but other features are similar to those of the sample collection implement S9. The movable member 4H is inserted into the container 1G to a position close to the lower end thereof, so that the movable member can slide in the up-down direction. The movable member has a through hole 47 having an opening closed by an auxiliary shielding material 48. The auxiliary shielding material 48 can be pierced by lowering a sample collection stick 2G.

A space 15a separated from the accommodation portion 10 of the liquid 5 by the movable member 4H is formed below the movable member 4H. Solid calcium peroxide 60 and a water-containing bag 61 are disposed as substances 6 for gas generation in the space 15a. The water-containing bag 61 has a bag body made from a flexible film that contains water. As shown in FIG. 18B, the distal end portion at the lower end of the sample collection stick 2G can be introduced into the space 15a and lowered to a height at which the water-containing bag 61 is pierced. Where the water-containing bag 61 is pierced, water flows therefrom to the outside and this water reacts with calcium peroxide 60, thereby generating oxygen. The pressure of the oxygen becomes a force moving the movable member 4H.

When the sample collection implement S10 of the present embodiment is used, the sample collection operation is similar to that performed with the above-described sample collection implement S9. Thus, in the state shown in FIG. 17, the sample collection stick 2G is taken out of the container 1G and a sample is collected in a sample collection portion 21a. Then, as shown in FIG. 18A, the sample collection stick 2G is inserted into the container 1G. During this insertion, the shielding material 9 is pierced by using the sample collection stick 2G and the sample collection portion 21a is dipped into the liquid 5. As a result, the sample diffuses into the liquid 5. When the sample is then examined, the sample collection stick 2G is further lowered as shown in FIG. 18B, whereby the auxiliary shielding material 48 is pierced, the distal end portion at the lower end of the sample collection stick 2G is introduced into the space 15a and the water-containing bag 61 is also pierced. As a result, as mentioned hereinabove, water that has flown out of the water-containing bag 61 reacts with the calcium peroxide 60, thereby generating oxygen, and the pressure of the oxygen rises the movable member 4H. As a result, the liquid 5 is pushed up by the movable member 4H and part of the liquid 5 passes upward through the filter 3G. The filtered liquid 5' is sucked in by the suction nozzle 8 that has pierced the cover sheet 28b and was inserted into the container 1G. The filtered liquid is then taken into an automatic analyzer.

In the sample collection implement S10 of the present embodiment, the filter 3G may be permanently fixed and a filter with a low mechanical strength can be used as the filter 3G, in the same manner as in the above-described sample collection implement S9. Since the movable member 4H is moved by using a gas pressure generated by a gas generating substance 6 accommodated inside the container 1G, it is not necessary to apply a pressure to the movable member 4H from the outside. The operation of generating a gas pressure by using the gas generating substance 6 may be performed by lowering the sample collection stick 2G, and the advantage of such an operation is that it is easy to perform and places but a small operation load on the person examining the sample.

Figure 19A:
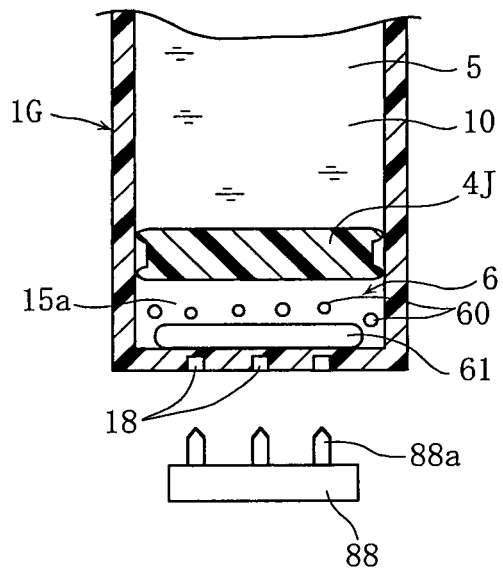
FIG. 19A is a principal cross-sectional view illustrating another example of a sample collection implement in accordance with the present invention.
Figure 19B:
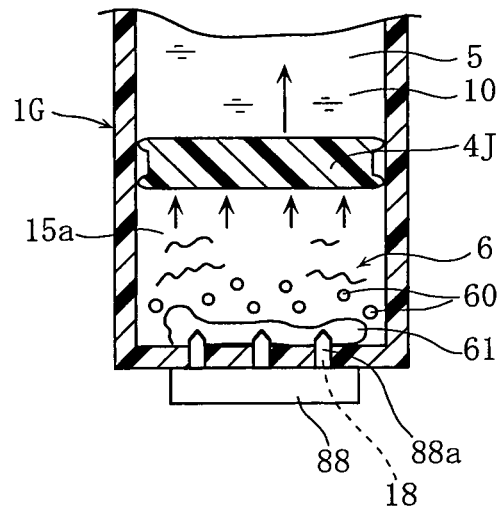
FIG. 19B is a principal cross-sectional view illustrating the usage state thereof.

In the embodiment shown in FIG. 19A, a member 88 provided separately from the container 1G is used as a means for rupturing a water-containing bag 61 accommodated in a space 15a inside the container 1G. The member 88 has one or a plurality of protruding portions 88a. Holes 18 that make it possible to rupture the portions to which a pressure is applied when the protruding portions 88a are inserted and pushed by a strong force are provided in the bottom portion of the container 1G. In order to perform the filtration of the liquid 5, the protruding portions 88a are introduced into the container 1G from the zones where the holes 18 are formed, as shown in FIG. 19B. As a result, the water-containing bag 61 is ruptured, the water is caused to react with calcium peroxide 60, oxygen is generated, and a movable member 4J is lifted. By contrast with the above-described sample collection implement S10, in the present embodiment, it is not necessary to lower the sample collection stick through a large stroke in order to reach the water-containing bag 61.

Figure 20:
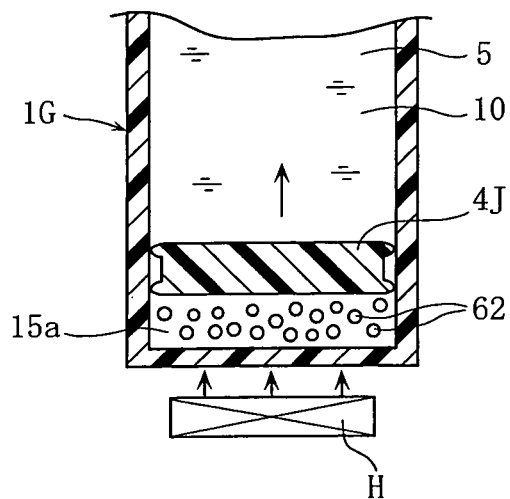
FIG. 20 is a principal cross-sectional view illustrating another example of a sample collection implement in accordance with the present invention.

In the embodiment shown in FIG. 20, sodium percarbonate 62 is accommodated as a gas-generating substance in a space 15a inside the container 1G. In the present embodiment, where the sodium percarbonate 62 is heated to a temperature equal to or higher than a predetermined temperature by using a heater H, the sodium percarbonate 62 is decomposed into sodium carbonate and hydrogen peroxide, and the hydrogen peroxide is then decomposed into water and oxygen. The movable member 4J can be raised by the oxygen pressure. As follows from the embodiments shown in FIGS. 17 to 20, a variety of substances can be used as the gas-generating substance in accordance with the present invention.

In the above-described sample collection implement of the third type, any element capable of generating a force that will move the movable member in the predetermined direction may be used as the power generating element in accordance with the present invention. Therefore, a means other that the above-described magnet (or non-magnetized ferromagnetic material) or gas-generating substance can be used.

[Sample Collection Implement of the Fourth Type]

The sample collection implement of the fourth type has a configuration in which a movable member and a sample collection stick are engaged and the movable member moves in conjunction with the operation of the sample collection stick. A predetermined liquid is caused by the movement of the movable member to pass through a filter.

Figure 21:
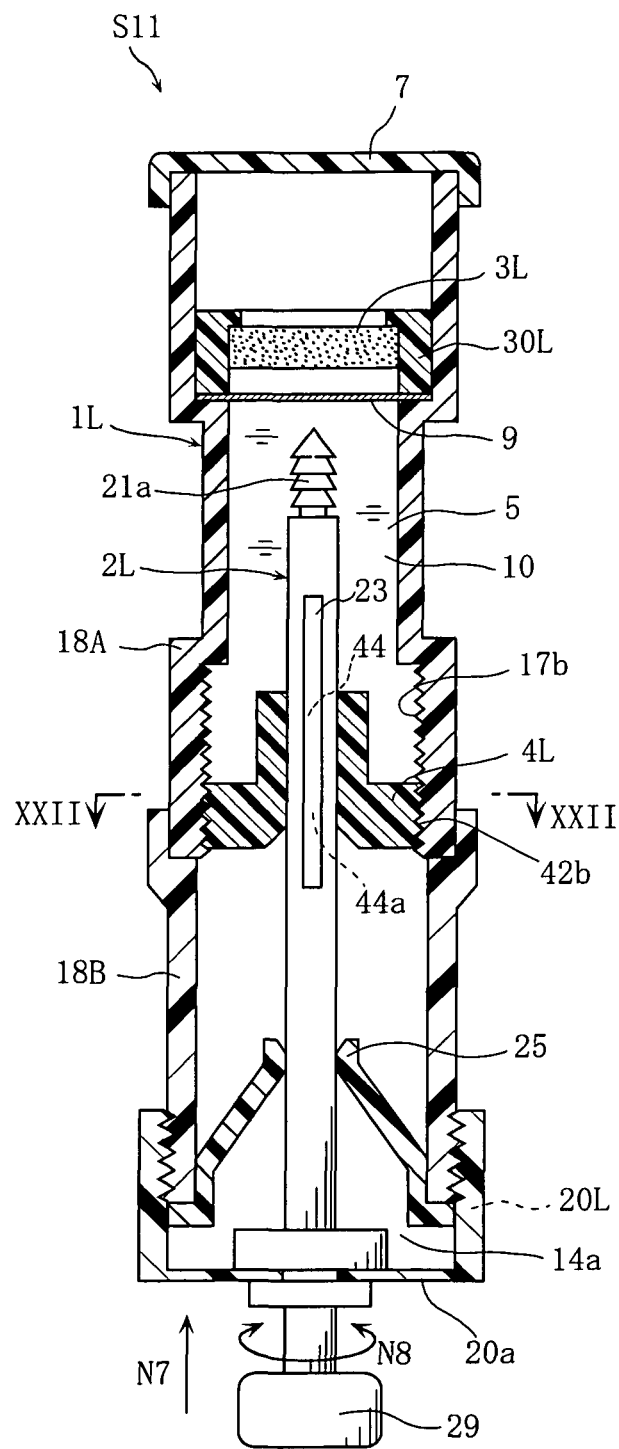
FIG. 21 is a cross-sectional view illustrating another example of a sample collection implement in accordance with the present invention.
Figure 22:
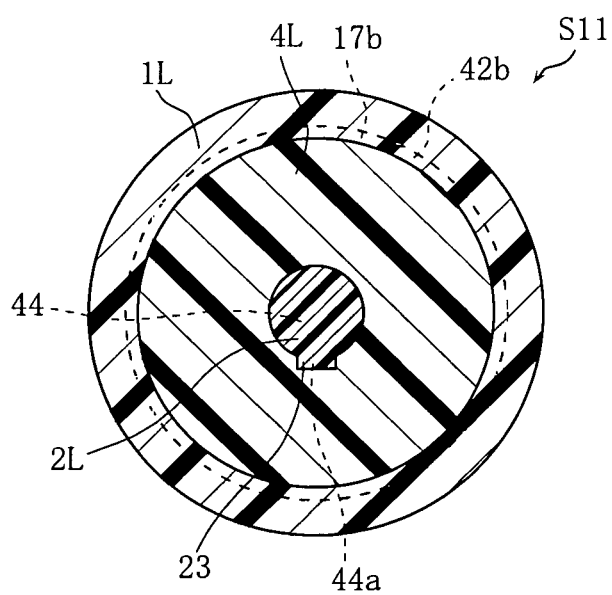
FIG. 22 is a XXII-XXII cross-sectional view of the configuration shown in FIG. 21.
Figure 23:
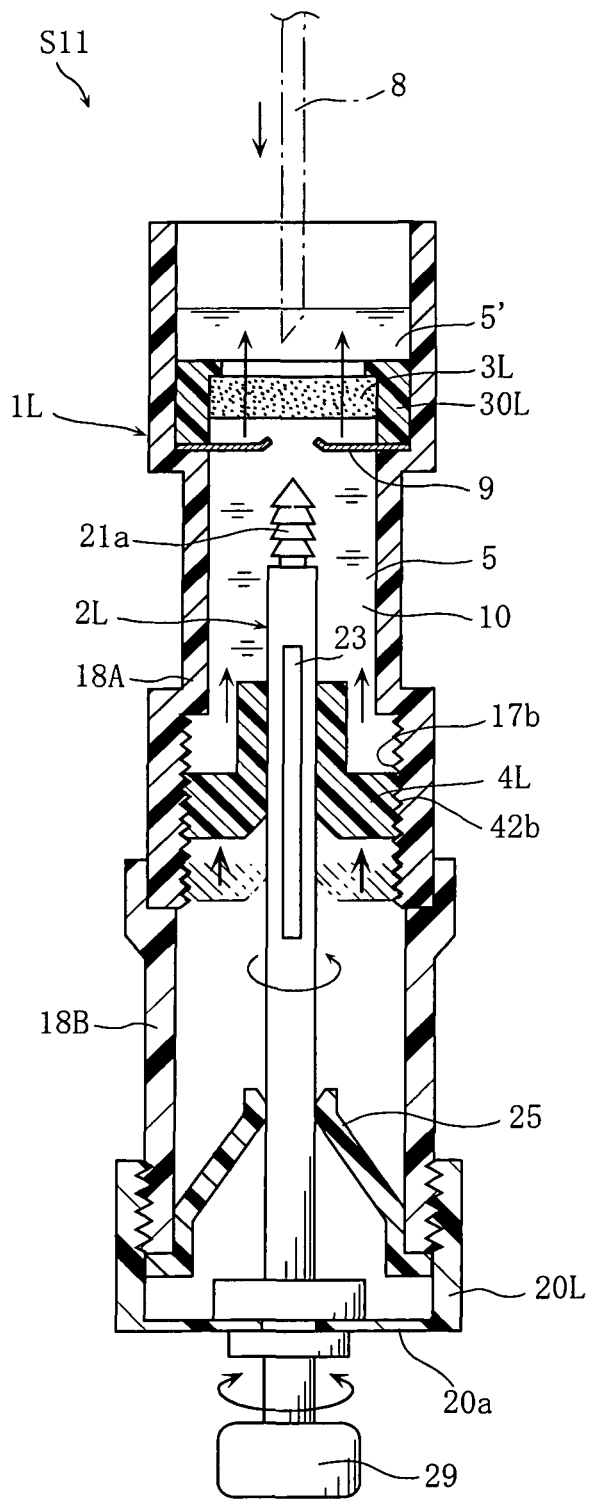
FIG. 23 is a principal cross-sectional view illustrating the usage state of the sample collection implement shown in FIG. 21.

FIGS. 21 to 23 show an example of the sample collection implement of the fourth type. As shown in FIG. 21, in a sample collection implement S11 of the present embodiment, a sample collection stick 2L passes through a movable member 4L, and when the sample collection stick 2L is rotated, the movable member 4L is lifted towards a filter 3L by a screw feed action of threaded portions 17b, 42b.

More specifically, a filter 3L held in a holder 30L is fixedly provided in the upper portion inside a container 1L, and a region below a shielding material 9 is provided below the holder 30L is an accommodation portion 10 of a liquid 5. A threaded portion 17b is formed at the inner circumferential surface in the central portion in the up-down direction of the container 1L. The container 1L is constricted by linking two cylindrical members 18A, 18B. With such a configuration, the threaded portion 17b can be easily formed at the inner circumferential surface of the container 1L. However, in a configuration different from that of the present embodiment, the container 1 can be formed as a single member. The movable member 4L serves to push the liquid 5 upward. A threaded portion 42b that is screwed into the threaded portion 17b is formed at the outer circumferential surface of the movable member, and a through hole 44 for inserting a sample collection stick 2L is provided in the central portion of the movable member.

The sample collection stick 2L is provided with an operation knob 29 positioned below a lid 20L, and the sample collection stick can be raised as shown by an arrow N7 and rotated as shown by an arrow N8 by operating the knob 29. The sample collection stick 2L is inserted into the through hole 44 of the movable member 4L so that the sample collection stick can slide in the up-down direction (axial direction of the sample collection stick 2L), and only the sample collection stick 2L can be lifted, while the movable member 4L stays fixed. Therefore, a shielding material 9 can be pierced by lifting only the sample collection stick 2L. However, relative rotation of the sample collection stick 2L and the movable member 4L is blocked. An engagement convex portion 23 extending in the up-down direction is formed as a means for blocking the relative rotation at the outer circumferential surface of the sample collection stick 2L, and this engagement convex portion 23 is engaged with a concave portion 44a in the form of a key groove that is formed at the inner circumferential surface of the through hole 44, as shown in FIG. 22. Obviously, instead of using the above-described configuration, it is also possible to form a polygonal cross-sectional shape of the shaft portion of the sample collection stick 2L and provide the through hole 44 with the polygonal shape corresponding thereto, thereby making it possible to obtain a configuration that blocks the relative rotation of the sample collection stick 2L and the movable member 4L. The threaded portion 17b of the container 1L, the movable member 4L, and the sample collection stick 2L constitute a screw feed mechanism that can move the movable member 4L in the up-down direction by rotating the sample collection stick 2L.

In order to conduct the examination of the sample after the sample has diffused into the liquid 5, the sample collection stick 2L is lifted and part of the shielding material 9 is ruptured. Then, the sample collection stick 2L is rotated in the predetermined direction. As a result, as shown in FIG. 23, the movable member 4L is lifted by the screw feed action of the threaded portions 17b, 42b and the liquid 5 is pushed up. As a result, part of the liquid 5 passes through the filter 3L upward. A liquid 5' that has thus been filtered is retained on the filter 3L and can be taken into a predetermined automatic analyzer by using a suction nozzle 8.

Thus, in the sample collection implement S11 of the present embodiment, it is not necessary to push the filter 3L directly with the suction nozzle 8 as a means for filtering the liquid 5, and a material with a low mechanical strength also can be used for the filter 3L. The operation of the sample collection stick 2L serving to move the movable member 4L involves gripping and rotating the knob 29 and such an operation can be easily performed. Since the movable member 4L is moved by using a screw feed mechanism, the movable member can moved reliably. Furthermore, the sample collection implement S11 should be anyway provided with the sample collection stick 2L that can also be effectively used as an operational member for moving the movable member 4L. Therefore, the sample collection implement has a rational configuration, and the increase in the number of parts can be reduced to a minimum.

FIGS. 24A and 24B illustrate another example of a sample collection implement of the fourth type.

In a sample collection implement S12 of the present embodiment. A movable member 4M is slidably inserted into a container 1M. A linking portion 20a of a lid 20 has high flexibility in the up-down direction, and the sample collection stick 2M can be lifted by a comparatively large stroke. The sample collection stick 2M is inserted into a through hole 44 of the movable member 4M. A convex engagement portion 22 is provided at the outer surface of the sample collection stick 2M in a portion close to the lower end of the movable member 4M, and when the sample collection stick 2M is lifted, this engagement portion 22 comes into contact with the lower surface portion of the movable member 4M and pushes the movable member 4M upward. A concave portion 39 that is open at a lower end is formed in the central portion of a holder 30M of a filter 3M. This concave portion 39 serves to avoid interference with the sample collection stick 2M when the sample collection stick 2M is lifted. Since the interference is avoided, the lift stroke of the sample collection stick 2M and the movable member 4M can be sufficiently increased. The filter 3M is formed in a ring-like shape and disposed around the concave portion 39.

In the sample collection implement S12, where the sample collection stick 2M is lifted by a large stroke, as shown in FIG. 24B, a shielding material 9 is ruptured and the movable member 4M is pushed by the engagement portion 22 and lifted. As a result, the liquid 5 is pushed by the movable member 4M and part of the liquid 5 passes through the filter 3M. A liquid 5' that has thus been filtered is retained on the filter 3M. Thus, in the sample collection implement S12, the liquid 5 can be caused to pass through the filter 3M by a simple configuration using the sample collection stick 2M, in the same manner as in the above-described sample collection implement S11. In the sample collection implement S12, it is not necessary to rotate the sample collection stick 2M and the sample collection stick may be lifted in a simple manner. Therefore, the operation of the sample collection implement is easier than that of the sample collection implement S11.

The present invention is not limited to the contents of the above-described embodiments. The design of specific configurations of parts of the sample collection implement in accordance with the present invention can be changed variously.

Although the sample collection implement in accordance with the present invention is advantageous for sampling feces, the type of samples is not limited to feces. Various substances such as clayish substances or soils close thereto can be also used as samples. A sample may be in the form of an aqueous solution. In this case, impurities can be removed by using a filter after the sample has been diluted with the liquid accommodated in the accommodation portion of the sample collection implement. Various liquids for suspending or diluting a sample and a variety of filters including the conventional or newly developed ones can be used, and specific components and materials thereof can be appropriately selected according to the sample type or sample examination contents. Specific shapes and materials of the movable member, container, and sample collection stick are not particularly limited.

The invention claimed is:

1. A sample collection implement comprising:
  a container having an accommodation portion in which a liquid for suspending or diluting a sample is accommodated, a sample collection stick being able to be disposed in the accommodation portion, and
  a filter provided inside the container,
  the sample collection implement further comprising
  a movable member that can be moved in a predetermined direction inside the container and has a function of pushing the liquid and causing the liquid to pass through the filter, when moved in the predetermined direction, wherein
  the movable member is provided separately from the filter and can be moved by being pushed from outside the container, and
  adjacent first and second regions partitioned by a partition wall are formed inside the container,
  the filter is disposed in the first region, and
  when the liquid passes through the filter by the movement of the movable member, at least part of the liquid that has passed through the filter flows into the second region over the partition wall, and is retained in the second region.

2. The sample collection implement according to claim 1, wherein
  the movable member is slidably inserted into the second region and can move down when pushed from above to push the liquid so as to cause the liquid to pass through the filter, and
  when the liquid that has passed through the filter flows into the second region, the liquid can be retained on the movable member.

3. The sample collection implement according to claim 1, wherein
  the movable member is provided in a location different from the second region, the second region has a form such that a bottom portion thereof is closed by part of the container or by a fixing member separate from the container, and when the liquid that has passed through the filter flows into the second region, the liquid can be retained on the bottom portion.

4. A sample collection implement comprising:

a container having an accommodation portion in which a liquid for suspending or diluting a sample is accommodated, a sample collection stick being able to be disposed in the accommodation portion, and a filter provided inside the container, the sample collection implement further comprising a knob, a movable member that exists within the container that can be moved in a predetermined direction inside the container and has a function of pushing the liquid and causing the liquid to pass through the filter, when moved in the predetermined direction, further comprising a linking means capable of linking the sample collection stick to the movable member in a state in which the sample collection stick is inserted into the container, wherein the filter is held by the movable member, the sample collecting stick is not linked to the movable member when the sample collecting stick is outside of the container, is used to collect a sample in this condition, and is linked to the moveable member through the linking means when the sample collection stick is inserted into the accommodation portion, and the movable member can be moved in the predetermined direction by operating the sample collection stick in a state in which the sample collection stick is linked to the movable member by the linking means.

5. The sample collection implement according to claim 4, wherein the linking means includes a pair of threaded portions provided at the movable member and the sample collection stick, and an advance operation of the sample collection stick towards the movable member and a rotation operation thereof can be performed in a state in which the sample collection stick is inserted into the container, and the pair of threaded portions can be screwed together by the operations.

6. The sample collection implement according to claim 4, wherein the linking means includes a concave portion provided in one of the movable member and the sample collection stick, and a convex portion that is provided in the other of the two and can be inserted into the concave portion when the sample collection stick is advanced towards the movable member, the concave portion has a constriction portion that is locally reduced in width, and the convex portion has a protruding portion that engages with the constriction portion to prevent the convex portion from slipping out of the concave portion after the convex portion is inserted into the concave portion.

7. A sample collection implement comprising:

a container having an accommodation portion in which a liquid for suspending or diluting a sample is accommodated, a sample collection stick being able to be disposed in the accommodation portion, and a filter provided inside the container, the sample collection implement further comprising a movable member that can be moved in a predetermined direction inside the container and has a function of pushing the liquid and causing the liquid to pass through the filter, when moved in the predetermined direction, further comprising a power generating element that is disposed inside the container and serves to generate a force that causes the movable member to move in the predetermined direction, wherein the power generating element can be actuated by a predetermined operation or action outside the container or by the operation of the sample collection stick.

8. The sample collection implement according to claim 7, wherein the power generating element is a magnet or a non-magnetized ferromagnetic material constituting at least part of the movable member, and the movable member can be moved in the predetermined direction by causing a magnetic force to act upon the magnet or the ferromagnetic material from the outside of the container or from the sample collection stick.

9. The sample collection implement according to claim 7, wherein the movable member is provided so as to form a space partitioned from the accommodation portion inside the container, and the power generating element is a substance for gas generation that is accommodated in the space, and the movable member can be moved in the predetermined direction by a gas pressure created when the substance for gas generation generates gas.

10. A sample collection implement comprising:

a container having an accommodation portion in which a liquid for suspending or diluting a sample is accommodated, a sample collection stick being able to be disposed in the accommodation portion, and a filter provided inside the container, the sample collection implement further comprising a movable member that can be moved in a predetermined direction inside the container and has a function of pushing the liquid and causing the liquid to pass through the filter, when moved in the predetermined direction, wherein the movable member can he engaged with the sample collection stick, an operation causing at least one action from among rotation and movement can be performed with respect to the sample collection stick in a state in which the sample collection stick is inserted into the container, and when the operation is performed and the sample collection stick acts, the movable member moves in the predetermined direction in conjunction with this action.

11. The sample collection implement according to claim 10, wherein an outer circumferential surface of the movable member and an inner circumferential surface of the container are provided with a pair of threaded portions that are screwed together, when the sample collection stick is inserted into the container, the sample collection stick assumes a state in which the sample collection stick is inserted into a through hole provided in the movable member, can move in the predetermined direction relative to the movable member, and is blocked from rotating relative to the movable member, and when the sample collection stick is rotated, the movable member can be moved in the predetermined direction by a screw feed action of the pair of threaded portions.

12. The sample collection implement according to claim 10, wherein the sample collection stick is inserted into a through hole provided in the movable member when the sample collection stick is inserted into the container, and when the sample collection stick is advanced in the direction of insertion into the container by a distance equal to or longer than a predetermined distance, the movable member and the sample collection stick are engaged together and the movable member advances in conjunction with the sample collection stick.

* * * * *